United States Patent
Beck et al.

(10) Patent No.: US 7,057,712 B2
(45) Date of Patent: Jun. 6, 2006

(54) ANALYSIS SYSTEMS DETECTING PARTICLE SIZE AND FLUORESCENCE

(75) Inventors: Tyler J. Beck, Vadnais Heights, MN (US); Peter P. Hairston, St. Paul, MN (US); Stanley L. Kaufman, New Brighton, MN (US)

(73) Assignee: TSI Incorporated, St. Paul, MN (US)

( * ) Notice: Subject to any disclaimer, the term of this patent is extended or adjusted under 35 U.S.C. 154(b) by 254 days.

(21) Appl. No.: 10/602,178

(22) Filed: Jun. 24, 2003

(65) Prior Publication Data

US 2004/0057050 A1 Mar. 25, 2004

Related U.S. Application Data

(60) Provisional application No. 60/391,135, filed on Jun. 24, 2002.

(51) Int. Cl.
*G01N 21/64* (2006.01)
*G01N 21/53* (2006.01)
*G01N 15/02* (2006.01)

(52) U.S. Cl. ............ 356/72; 356/73; 356/318; 356/336; 356/338; 250/288; 250/461.1

(58) Field of Classification Search .......... 356/72, 356/73, 317, 318, 336, 338; 250/281, 288, 250/458.1, 459.1, 461.1, 461.2
See application file for complete search history.

(56) References Cited

U.S. PATENT DOCUMENTS

| | | | |
|---|---|---|---|
| 3,946,239 A | 3/1976 | Salzman et al. ............ 250/461 |
| 4,341,993 A | 7/1982 | Brunsting et al. ............ 324/71 |
| 4,943,159 A | 7/1990 | Oetliker et al. ............ 356/73 |
| 5,110,204 A | 5/1992 | Miles et al. ............ 356/28 |
| 5,127,729 A | 7/1992 | Oetliker et al. ............ 356/317 |
| 5,681,752 A | 10/1997 | Prather ............ 436/173 |
| 5,701,012 A | 12/1997 | Ho ............ 250/461.2 |
| 5,721,613 A | 2/1998 | Linowski et al. ............ 356/318 |
| 5,999,250 A * | 12/1999 | Hairston et al. ............ 356/318 |
| 6,532,067 B1 * | 3/2003 | Chang et al. ............ 356/318 |

OTHER PUBLICATIONS

Single Particle Detector Method and Apparatus using Light Scattering Techniques; 3308.7-US-01.

* cited by examiner

*Primary Examiner*—F. L. Evans
(74) *Attorney, Agent, or Firm*—Larkin Hoffman Daly & Lindgren Ltd.; Frederick W. Niebuhr, Esq.

(57) ABSTRACT

Particle analyzing systems with fluorescence detection are disclosed, primarily in connection with particle sizing based on scattered light intensity or time-of-flight measurement. In one system, emission of fluorescence is used as a threshold for selecting particles for further analysis, e.g. mass spectrometry. In another embodiment, laser beams arranged sequentially along an aerosol path are selectively switched on and off, to increase the useful life of components, and diminish the potential for interference among several signals. Other embodiments advantageously employ color discrimination in aerodynamic particle sizing, single detectors positioned to sense both scattered and emitted fluorescent radiation, and laser beam amplitude or gain control to enhance the range of fluorescence detection.

71 Claims, 16 Drawing Sheets

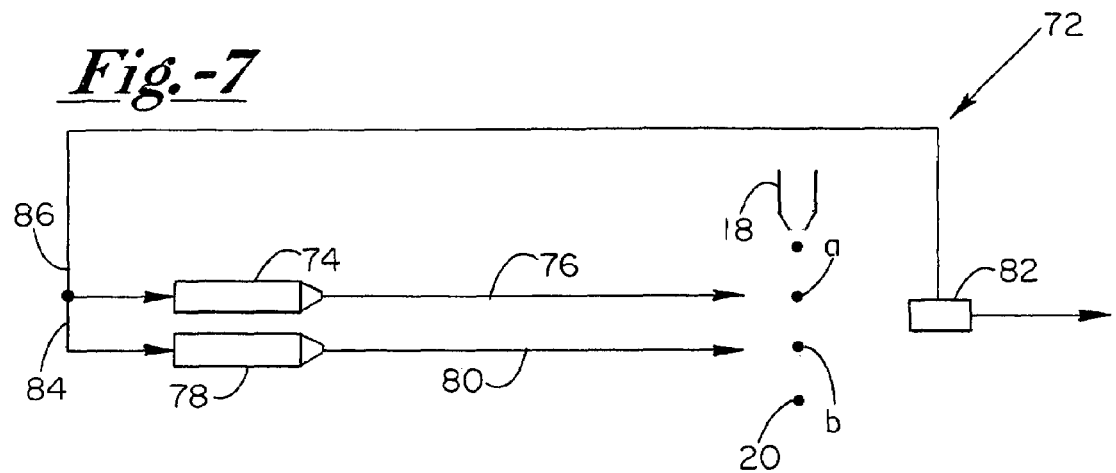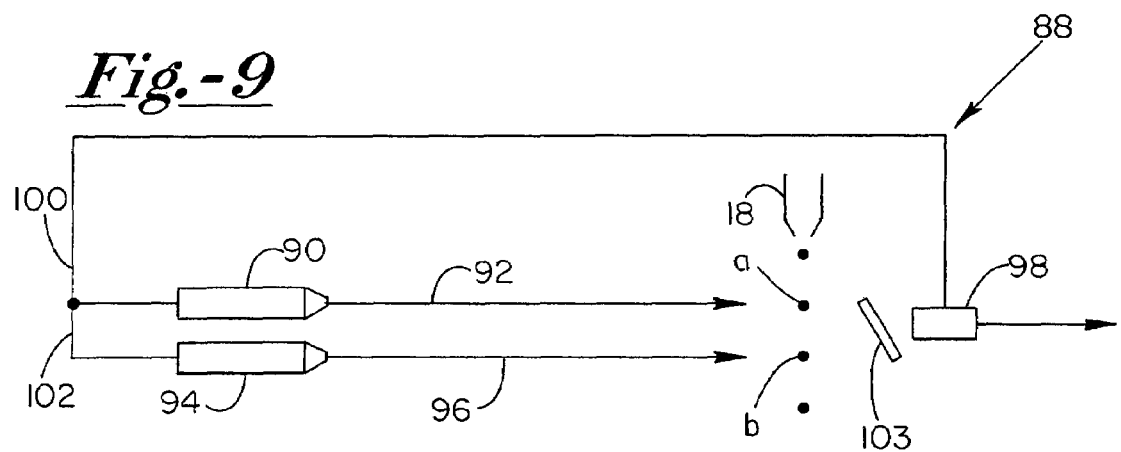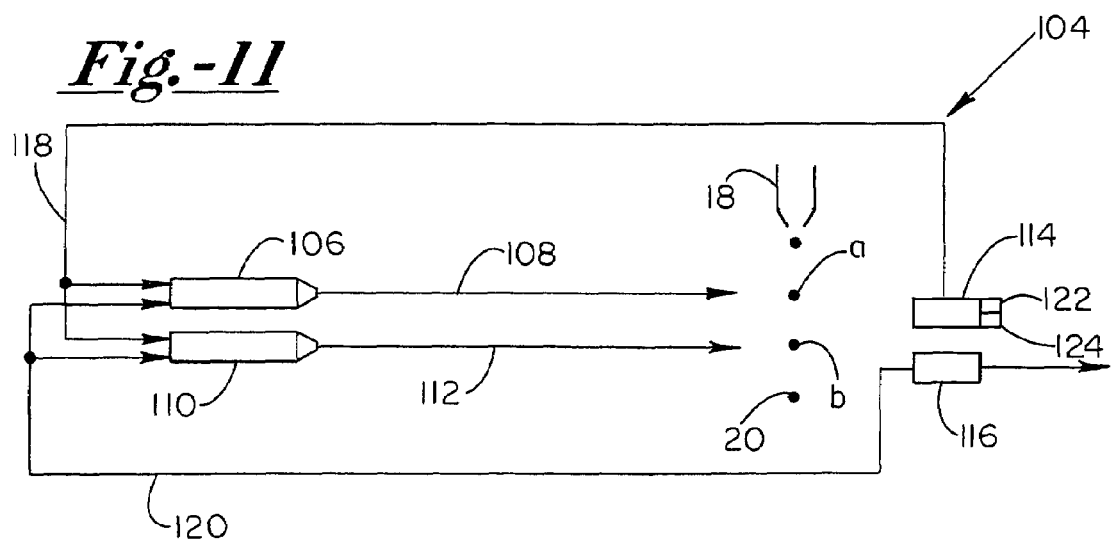

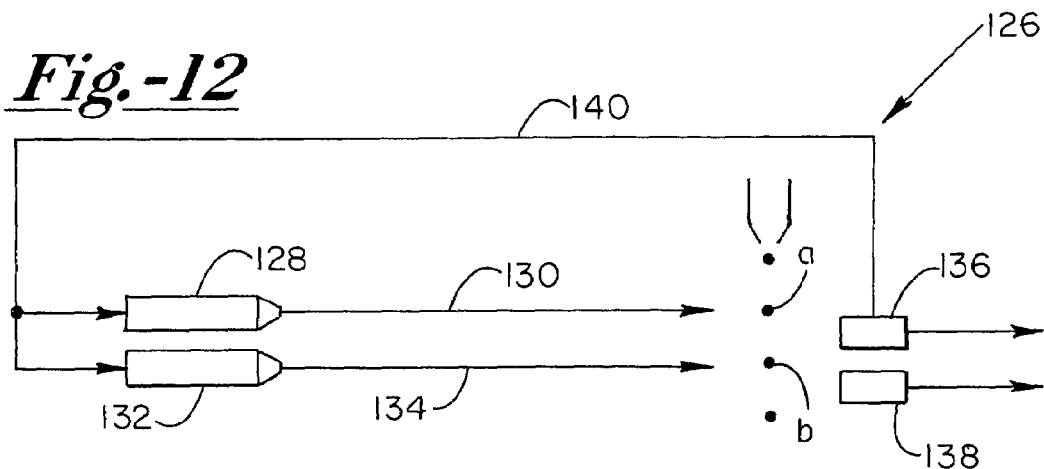
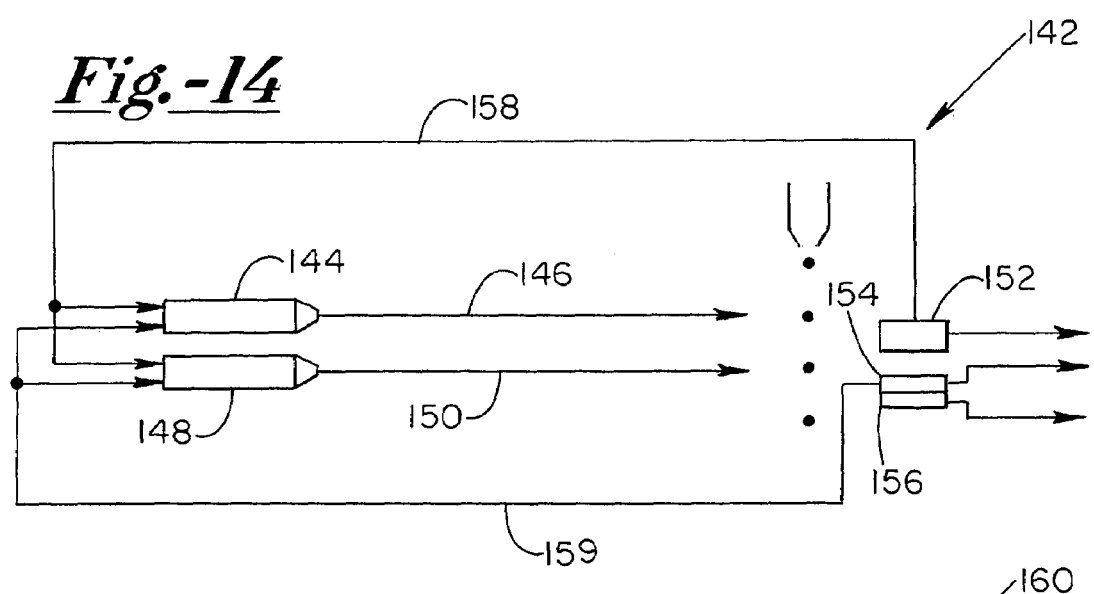
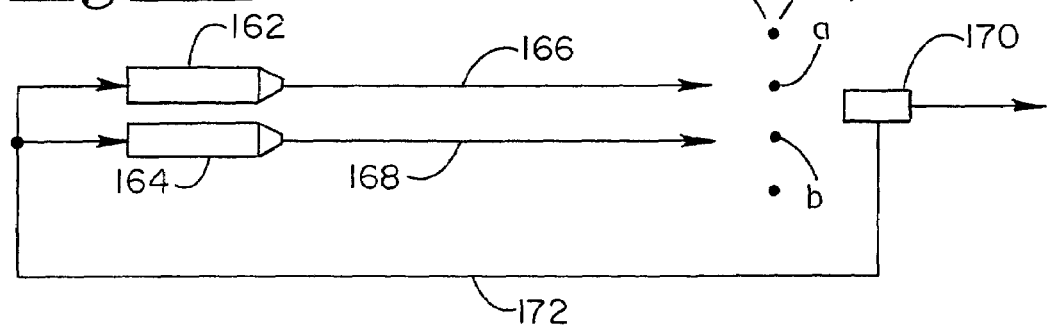

ANALYSIS SYSTEMS DETECTING PARTICLE SIZE AND FLUORESCENCE

This application claims the benefit of priority based on Provisional Application No. 60/391,135 entitled "Using Switched Light Sources for Fluorescence Detection and Aerodynamic Sizing," filed Jun. 24, 2002.

BACKGROUND OF THE INVENTION

The present invention is related to systems for detecting fluorescing particles in a fluid stream, for example as disclosed in U.S. Pat. No. 5,999,250 (Hairston, et al.), incorporated by reference herein. These systems involve directing focused beams of coherent energy onto an aerosol stream at various points along the stream. In particular, two red or near infrared beams in a continuous wave (CW) mode intersect the stream at spaced-apart points, impinging upon particles to generate time-of-flight measurements. An ultraviolet (UV) excitation beam is directed onto the particles downstream, to trigger fluorescence or other responsive emissions by the particles. The UV beam is operated in an on/off mode, triggered to irradiate a particle based on the time-of-flight signal generated by that particle when passing through the longer wavelength beams. Thus, time-of-flight measurements are used both to aerodynamically size the particles and to time each firing of the UV laser.

The present invention is directed to a variety of improvements in these systems, either to simplify the approach and reduce cost yet provide the same level of performance, or to enhance system performance by increasing detection sensitivity, enhancing component life, providing more complete information concerning particle composition, or to eliminate a potential source of time-of-flight measurement uncertainty.

The tendency of biological materials to emit fluorescence energy in response to irradiation by shorter wavelength energy, particularly in the violet and UV ranges, has been usefully employed in single particle analysis systems to detect the presence of biological agents in aerosols. Although specific biological materials differ from one another as to the most effective (peak) excitation wavelength, and as to the wavelengths of emitted fluorescent energy, it remains difficult to differentiate microbiological substances from oils, greases, volatile organic compounds and other ambient background particles, and more so to distinguish biological components from one another. Although this difficulty can be countered by combining other analysis techniques (e.g. mass spectrometry) with fluorescence detection, such combinations can present their own problems. For example, the ablation and ionizing laser in a time-of-flight mass spectrometer requires time between successive firings, to the point of reducing the speed of the overall system. In some situations, the reduced speed may be no more than an inconvenience. In systems designed to detect potentially harmful biological agents in a building ventilation system, the reduced rate may have a critical negative impact.

A concern applicable to all single particle analysis systems is the need for increasing the life of system components, especially the diode lasers and other radiant energy sources. In smaller, more compact systems, a further need arises to overcome the tendency of proximate radiation sources, and the energy scattered or emitted by particles exposed to these sources, from interfering with one another. Finally, there is a need to address the foregoing problems, and at the same time reduce system cost and complexity.

SUMMARY OF THE INVENTION

In accordance with the present invention, systems can be simplified by reducing the number of lasers or laser beams employed, the number of detectors, or the number of filters and other optical discrimination components, and by eliminating the need for certain components (e.g. beam splitters) used to generate the coherent energy. Sensitivity and efficiency are enhanced by selectively controlling system lasers, for example by triggering an increase in laser power responsive to sensing a particle, or by selectively activating or deactivating lasers in response to sensing a particle. As an additional benefit of this selective control, the useful life of each laser and associated components is increased. Several of the systems employ two different wavelengths of coherent energy, both of which are capable of stimulating fluorescence when impinging upon the particles under study. Accordingly, more information about particle composition can be obtained. In addition, the use of two different wavelengths, regardless of whether both are capable of stimulating fluorescence, enhances time-of-flight measurements by providing unambiguous beginning and ending measurement points.

One aspect of the present invention is a process for analyzing particles, including the following steps:

a. moving multiple particles serially along a predetermined path;

b. irradiating each particle with excitation energy as it traverses the path, wherein the excitation energy comprises energy at a first excitation frequency selected to cause a responsive emission depending on particle composition;

c. in connection with each irradiation of a particle, sensing for a responsive emission to determine an emissive response profile associated with the particle; and d. selecting, for further analysis, only the particles associated with emissive. response profiles that coincide with a predetermined reference profile.

In its simplest form, the emissive response profile can be the presence or absence of a fluorescent energy emission in response to the excitation radiation, which typically is in the violet or UV range. A reference profile can be more confined, for example to require fluorescent emissions within a predetermined range of wavelengths. The tendency of substances to emit different wavelengths of fluorescence in response to UV or violet excitation can be used to further refine the reference profile toward more specific identification of biological constituents. Yet another enhancement involves using several different UV or violet wavelengths to excite a given particle, in which event the reference profile can take into account the emissive tendencies of certain substances with respect to the different excitation wavelengths. If desired, one or more profiles are created based on tests with particles of a known composition. Then, the profiles can be used to test particles of unknown composition. Profiles can be created based on the presence of fluorescent emissions per se, or based on amplitudes of such emissions at various wavelengths. In addition, profiles may be based in part on particle size information. Finally, although this approach typically looks to the presence of fluorescent energy wavelengths or ranges, the absence of fluorescence at a particular wavelength may be employed as a determining factor within a given profile.

In accordance with this aspect of the invention, any one of several system embodiments can be augmented with a mass spectrometer at a point downstream of the laser beams. In a preferred embodiment, such system includes a time-of-flight mass spectrometer in which a UV laser ablates the particles under study, and ionizes molecules released by the ablation. An electric field accelerates the resulting ions, and time-of-flight measurements are used to identify particular ions. A primary advantage of this combination is the ability to select a subset of the particles in an aerosol stream for analysis by mass spectrometry, based on the preceding fluorescence detection.

A related aspect of the invention is a system for analyzing particles. The system includes a flow generating device for moving a particle-containing fluid along a designated path to carry the particles serially along the dedicated path. An excitation component provides excitation energy comprising energy at a first excitation frequency selected to cause a responsive emission depending on particle composition, and for irradiating the particles individually as they traverse the designated path. A sensing component is adapted to detect responsive emissions, and is operative in response to each irradiation of a particle to determine an emissive response profile associated with the particle. A selecting component is adapted to select for further analysis only the particles with associated emissive response profiles that coincide with a predetermined reference profile.

A further aspect of the present invention is a process for characterizing particles with controlled coherent energy sources, including the following steps:

a. moving multiple particles serially along a predetermined path;

b. generating a first coherent energy beam using a first source operable to adjust the first beam between a first state comprising a high amplitude operating mode and a second state comprising either a low amplitude operating mode or an inactive state;

c. generating a second coherent energy beam using a second source operable to adjust the second beam between a first state comprising a high amplitude operating mode and a second state comprising either a low amplitude operating mode or an inactive state;

d. while maintaining the first beam primarily in the first state, causing the first beam to intersect the predetermined path at a first location to irradiate each particle as it travels past the first location;

e. causing the second beam to intersect the predetermined path at a second location downstream of the first location, whereby the second beam is positioned to irradiate each particle as it passes the second location;

f. with respect to each particle, detecting a first response comprising radiant energy emanating from the particle in response to irradiation by the first beam; and g. responsive to detecting the first response, and before the particle reaches the second location, operating the first source to switch the first beam from the first state to the second state.

In a particularly advantageous approach, an upstream laser for scattering detection (first source) and a downstream laser for fluorescence detection and perhaps for scattering detection as well (second source), are both selectively switched between on/off states, or high amplitude/low amplitude states in response to upstream detection (typically scattered light) and downstream detection (frequently fluorescent emissions). Downstream detection resets the first and second sources, to "on" and "off," respectively. This approach enhances the useful life of both lasers, and prevents adjacent signals from interfering with one another. Consequently, the system can be more compact, and timing resolution is improved.

A related aspect of the invention is a particle characterizing apparatus with controllable coherent energy sources. The apparatus includes a flow generating device for moving a particle-containing fluid along a designated path to carry the particles serially along the path. A first source is adapted to generate a first coherent energy beam positioned to intersect the designated path at a first location for a first irradiation of each particle as it travels along the path. The first source is operable to adjust the first beam between a first state comprising a high amplitude operating mode, and a second state comprising either a low amplitude operating mode or an inactive state. The first source is further adapted to maintain the first beam primarily in the first state. A second source is adapted to generate a second coherent energy beam positioned to intersect the designated path at a second location downstream from the first location for a second irradiation of each particle as it travels along the path. The second source is operable to adjust the second beam between a first state comprising a high amplitude operating mode, and a second state comprising either a low amplitude operating mode or an inactive state. A sensing component is provided for detecting a first response comprising radiant energy emanating from the particle in response to the first irradiation, and adapted to generate a first signal upon such detecting. A control channel is coupled to the sensing component to receive the first signal, and coupled to the first source. The control channel is adapted to cause the first source to switch the first beam from the first state to the second state in response to receiving the first signal.

Another aspect of the present invention is a particle detection apparatus. The apparatus includes a flow generating device for moving multiple particles serially along a predetermined path. A coherent energy source is provided for causing a first beam having a first wavelength to intersect the predetermined path at a first location. A coherent energy source is provided for causing a second beam to intersect the predetermined path at a second location. The second beam has a second wavelength less than the first wavelength, selected to trigger a responsive emission dependent on particle composition. A detector is disposed proximate the predetermined path to detect energy at the first wavelength scattered by the particle as it travels past the first location, and to detect energy including a third wavelength emitted by the particle in response to irradiation by the second beam as it travels past the second location; wherein the third wavelength is longer than the second wavelength.

Devices constructed in accordance with this aspect of the invention can be more compact and simplified, in that single detectors are capable of performing dual or multiple detection functions. In these devices it is advantageous to carefully select the detectors with reference to their ranges of wavelength sensitivity. For example, a detector that is sensitive to violet and fluorescent wavelengths, but substantially insensitive to UV radiation, can be employed in a system to measure scattered light in the violet range, and light emitted in response to UV stimulation, while not influenced by scattered UV energy.

Yet another aspect of the present invention is a process for dynamically controlling sensor output in an aerosol characterizing system including a first radiant energy beam irradiating aerosol particles at a first location along a path, a second radiant energy beam for irradiating the aerosol particles as they travel past a second location downstream of the first location, a first sensor adapted to detect energy scattered by the particles as they pass the first location and to generate a first sensor output that varies with the intensity of scattered energy, and a second sensor for detecting fluorescent energy emitted by each particle at the second location in response to irradiation by the second beam and for generating a second output that varies with intensity of the fluorescent energy. The process for dynamically controlling the second sensor output includes:

a. detecting an amplitude of the first sensor output;
b. detecting an amplitude of the second sensor output;
c. detecting an amplitude of the second beam; and either:
(i) reducing the amplitude of the second beam, in response to detecting the first sensor output at an amplitude that exceeds a given maximum;
(ii) reducing a gain of the second sensor, in response to detecting the first sensor output at an amplitude that exceeds the given maximum; or
(iii) increasing an amplitude of the second beam according to a substantially linear ramp function while simultaneously monitoring a selected one of the second sensor output and the second beam amplitude, and clamping the ramp function when reaching a given maximum associated with the selected one.

In accordance with this aspect of the invention, the useful range of a fluorescence detector is considerably enhanced.

A further aspect of the present invention is a particle sizing system. The system includes a flow generating device for moving multiple particles serially along a predetermined path and causing the particles to accelerate along at least part of the path. A coherent energy source is provided for causing a first beam to intersect the predetermined path at a first location. A coherent energy source is provided for causing a second beam to intersect the predetermined path at a second location spaced apart from the first location. A first sensor is positioned to detect energy at the first wavelength emanating from the particle in response to irradiation by the first beam as it travels past the first location. A second sensor is positioned to detect energy emanating from the particle in response to irradiation by the second beam as it travels past the second location. The second wavelength is different from the first wavelength. A timing component is provided for determining a time for the particle to travel between the first and second locations, based on the outputs of the first and second detectors. The timing component is adapted to identify the output of an upstream one of the first and second detectors as a time measurement starting point and to identify the output of the other of the sensors as a time measurement ending point, based on the different wavelengths of the energy detected by the first and second sensors, respectively.

In single particle analysis systems that employ spaced-apart lasers for aerodynamic sizing, high particle concentrations present the risk that a second particle will enter the space between the lasers, before the immediately preceding first particle exits that space. The result is an ambiguity, due to the potential for misinterpreting the signal generated by the second particle's entry as an exit signal of the first particle. According to the present aspect of the invention, this problem is overcome by providing unambiguous, color-differentiated starting and ending signals for each time-of-flight measurement. Time-of-flight measurements can be based on energy emanating from the particles, whether scattered or emitted.

IN THE DRAWINGS

For a further understanding of the present invention and its advantages, reference is made to the following detailed description and to the drawings, in which.

Figure 5:
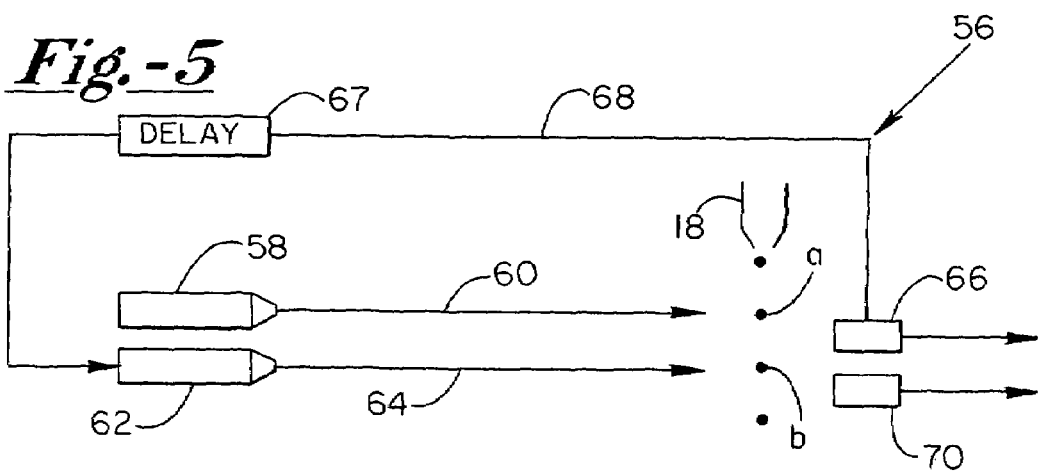
Figure 6:
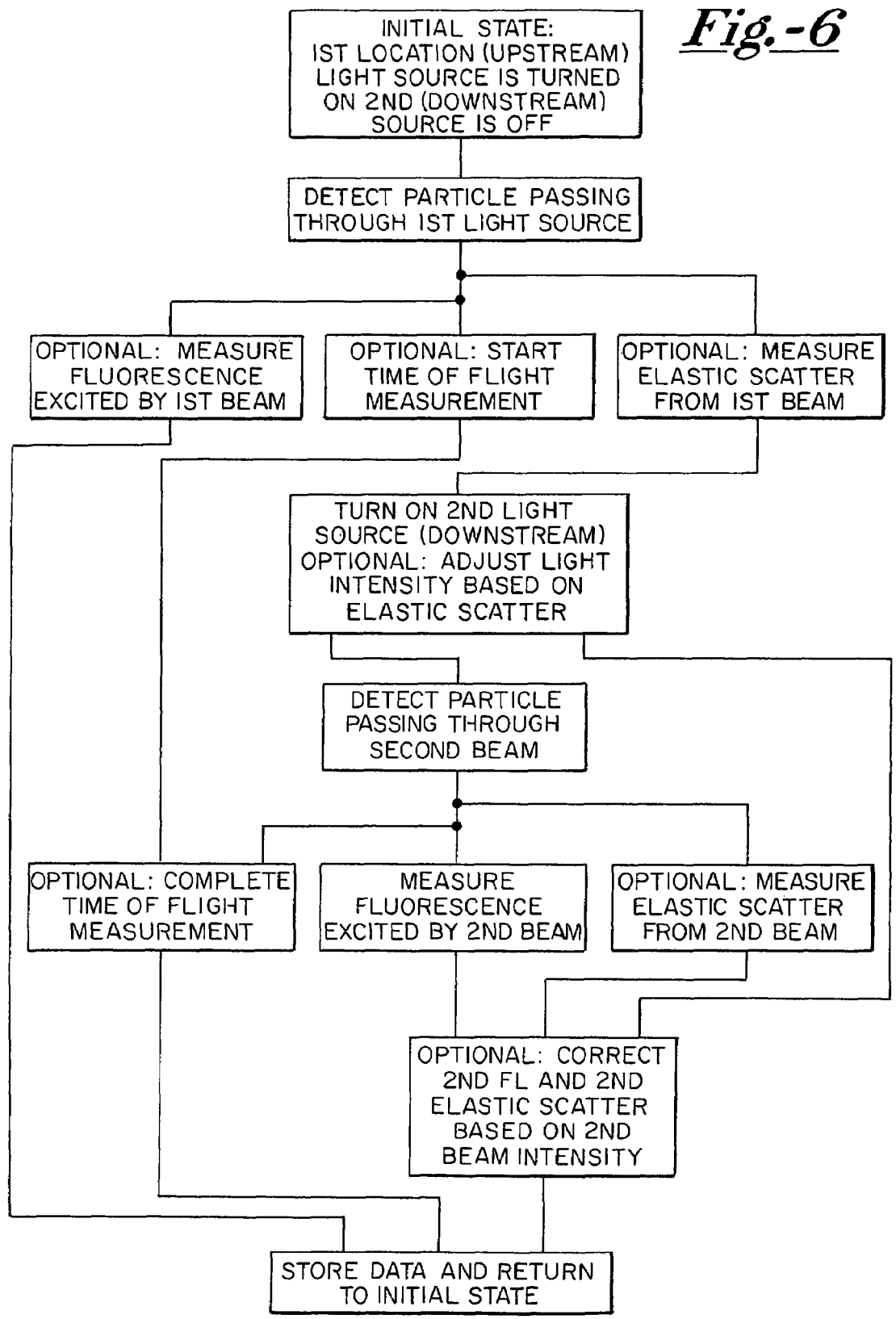
Figure 8:
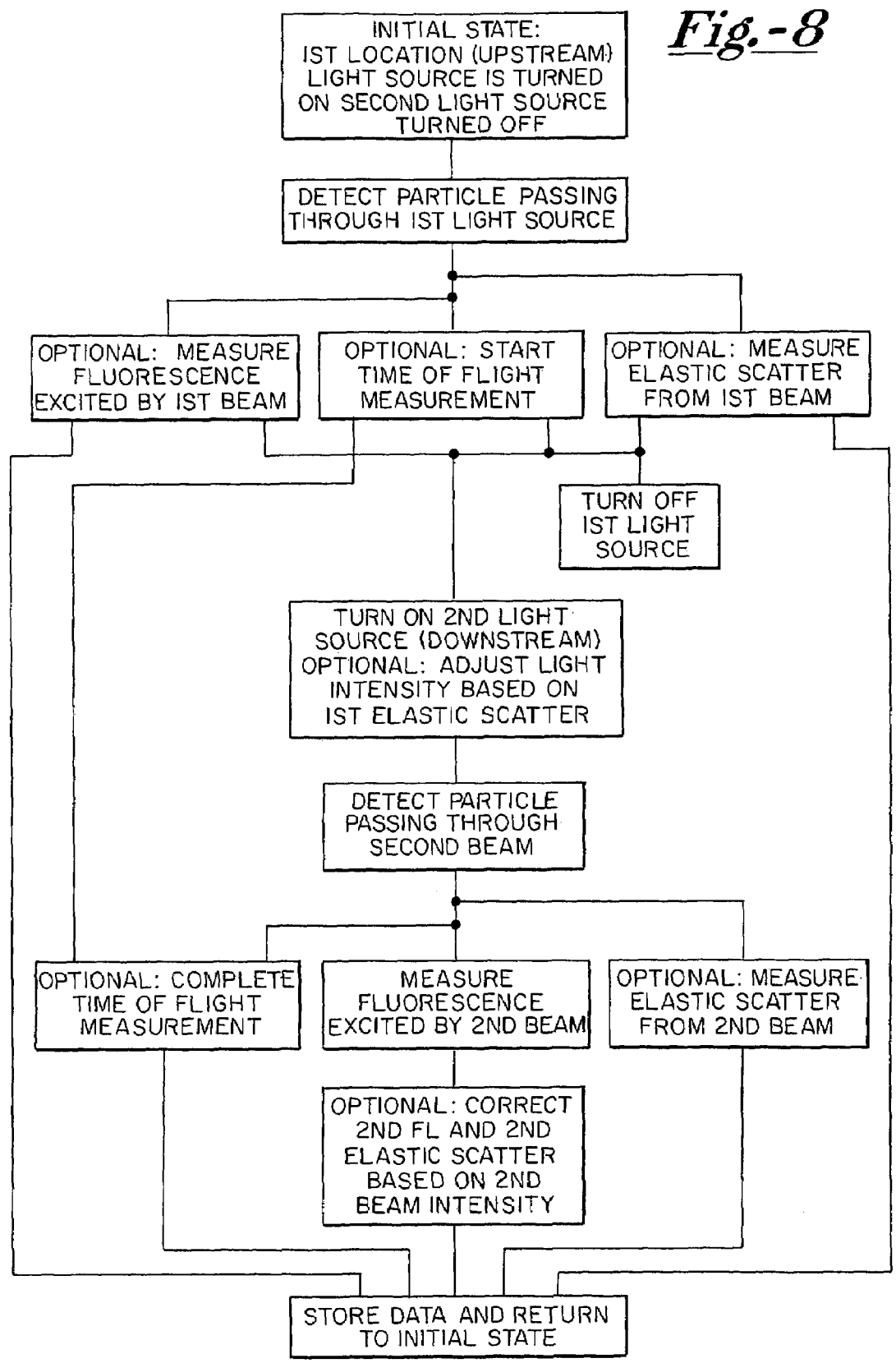
Figure 10:
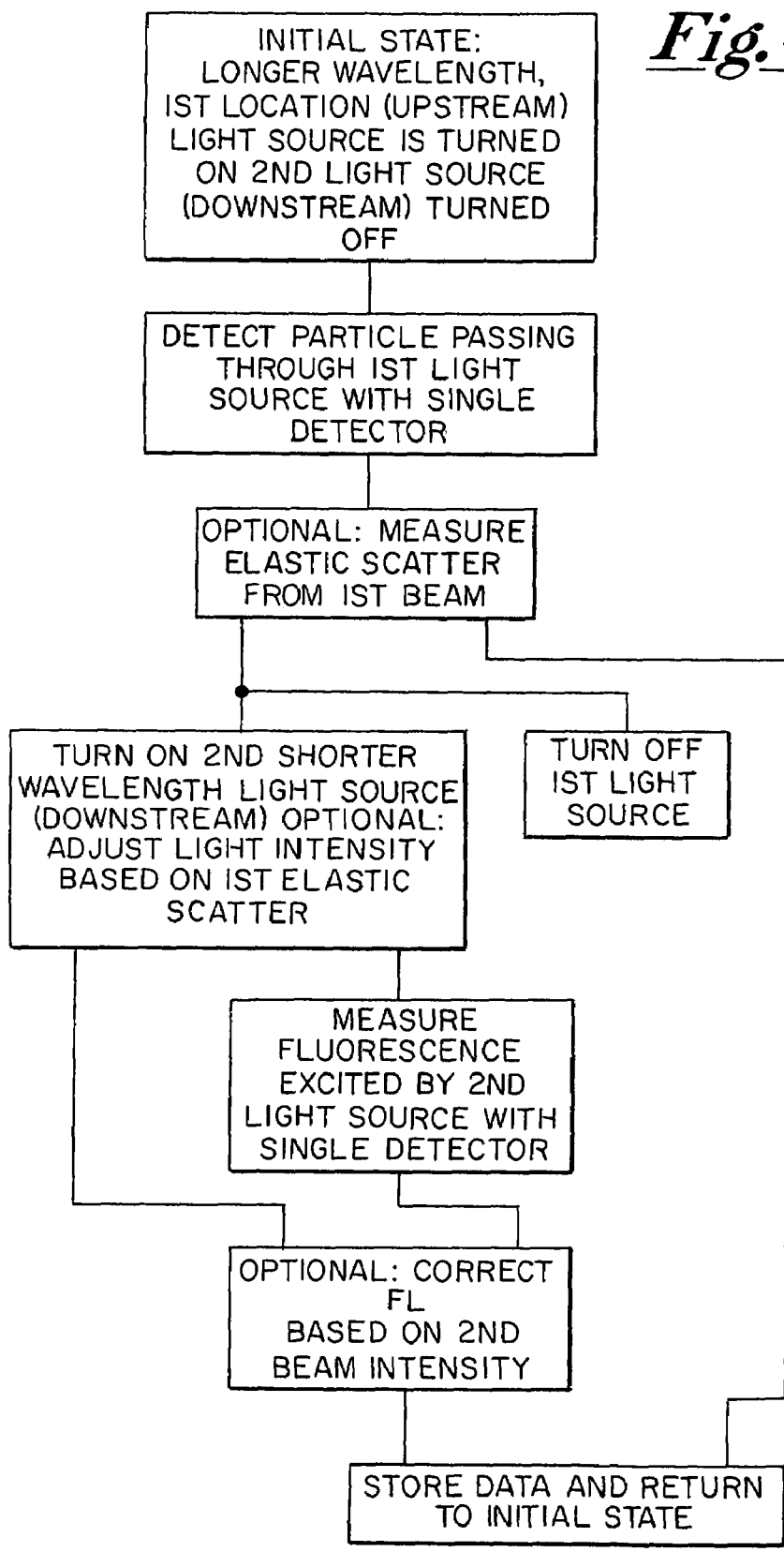
Figure 13:
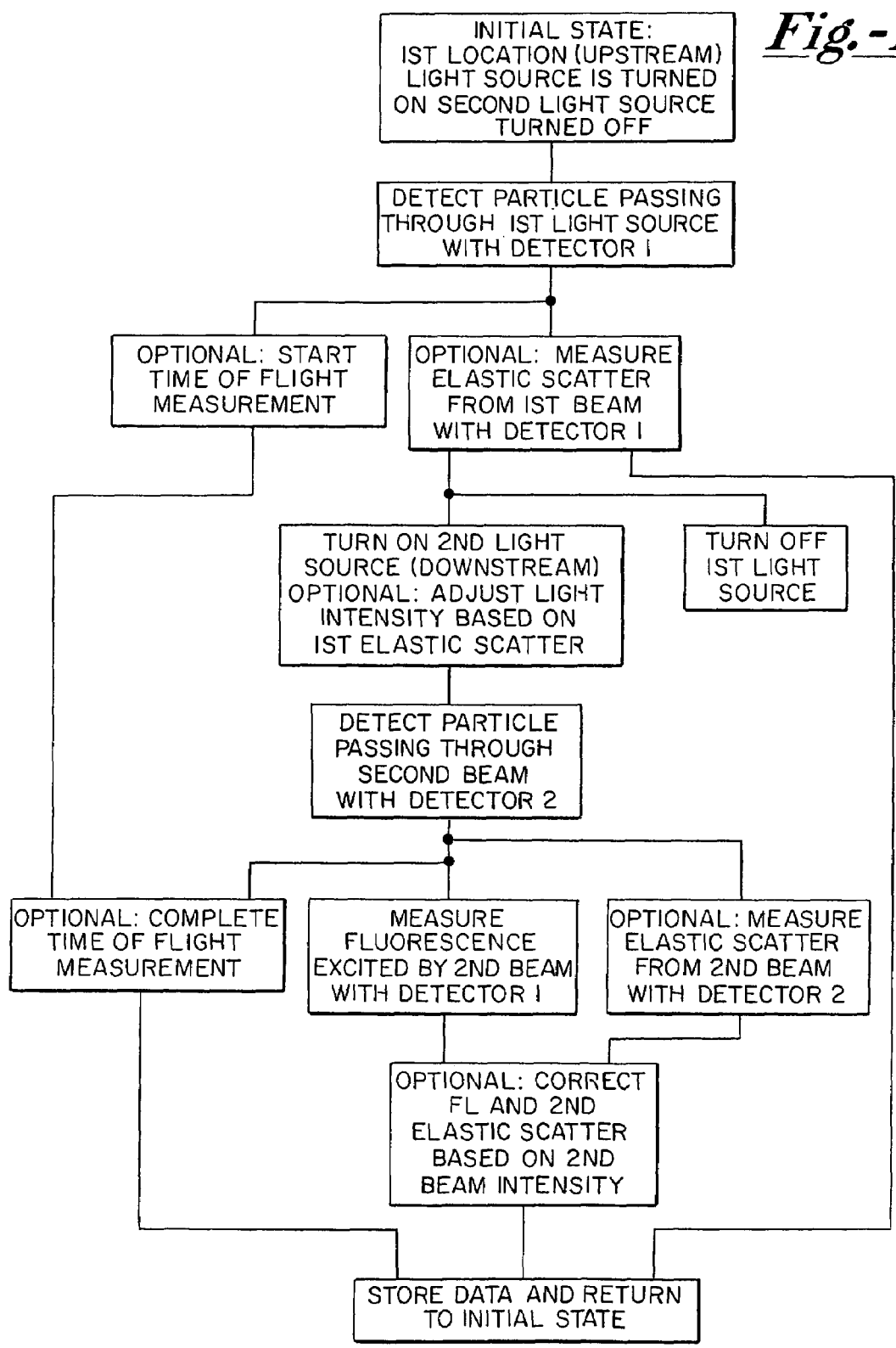
Figure 15:
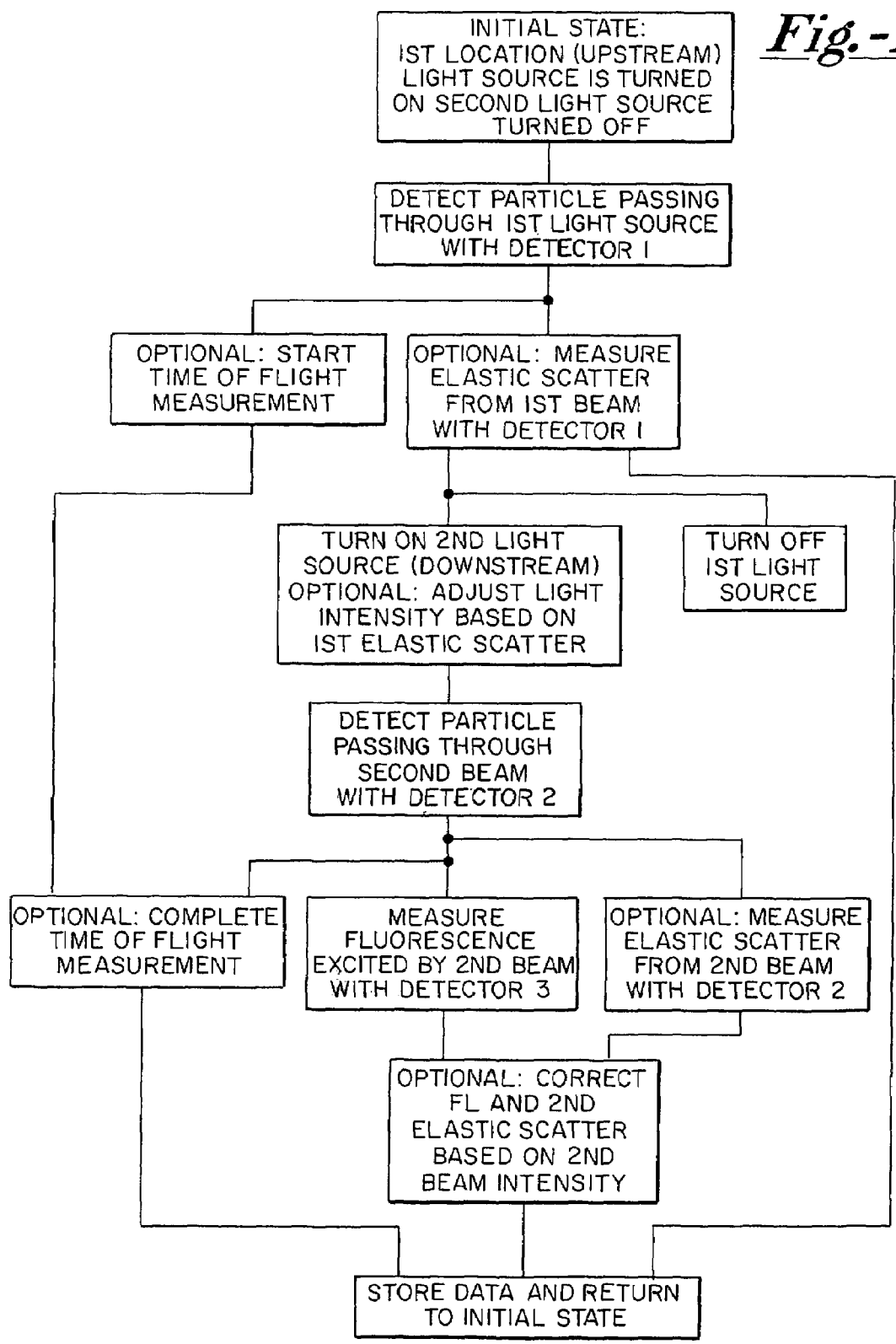
Figure 17:
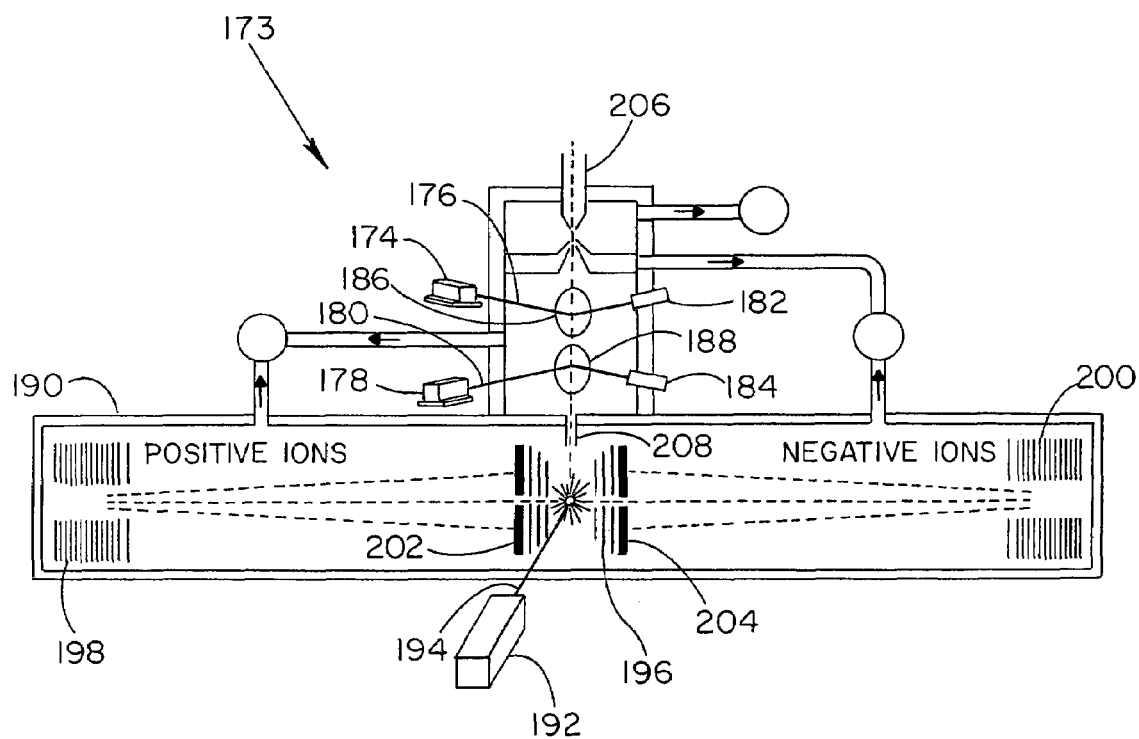
Figure 18:
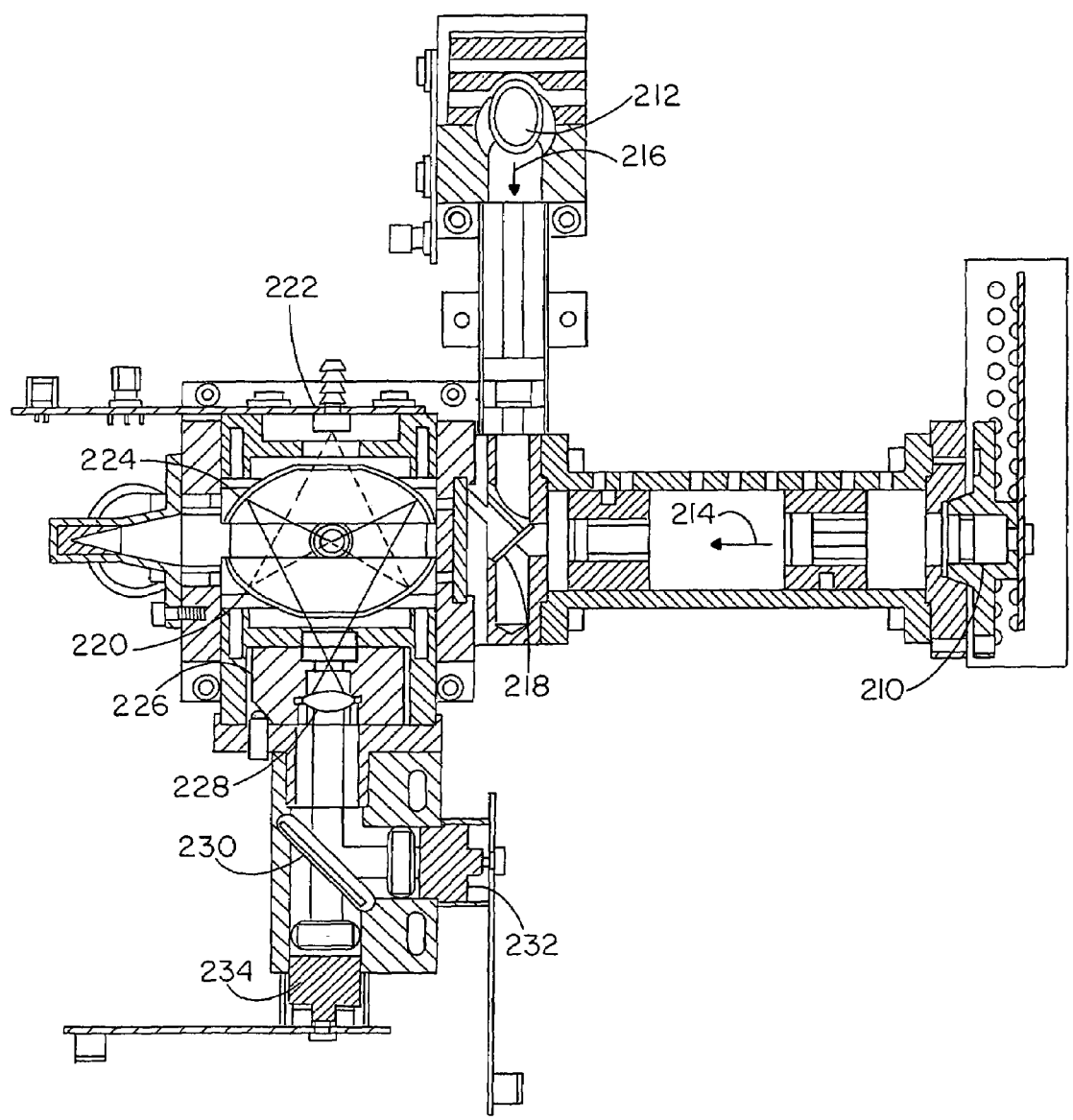
Figure 19:
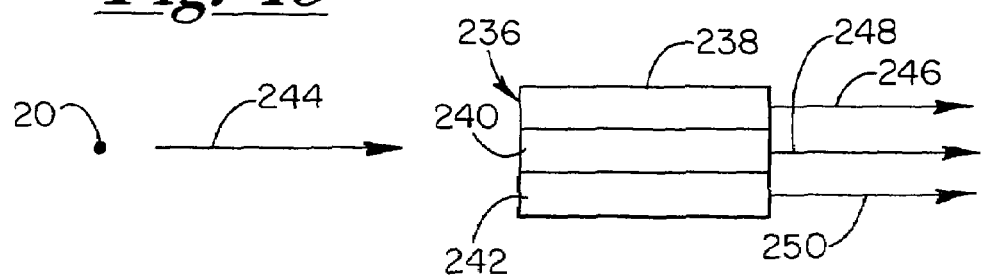
Figure 20:
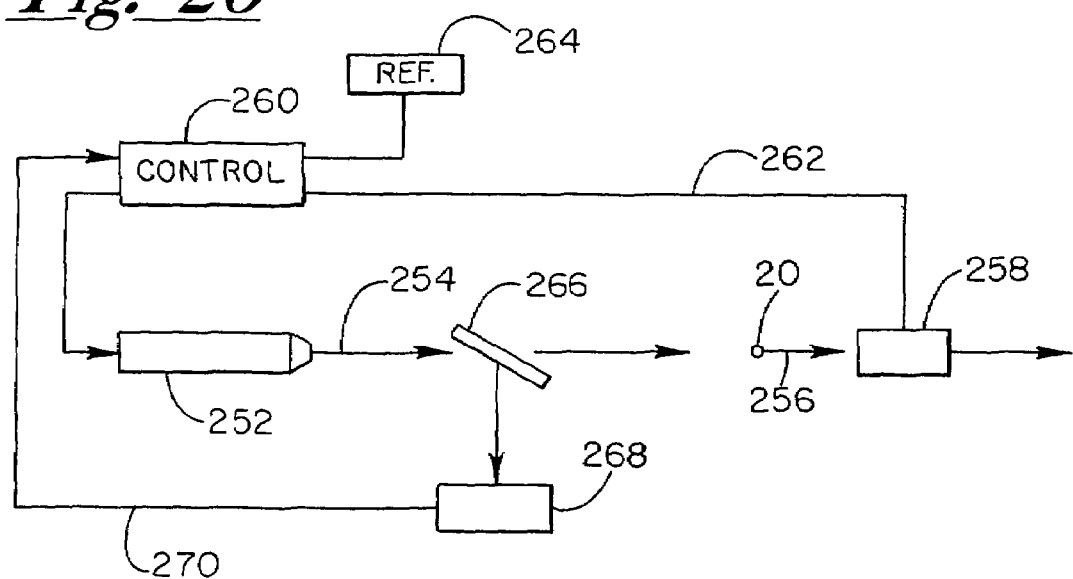
Figure 21:
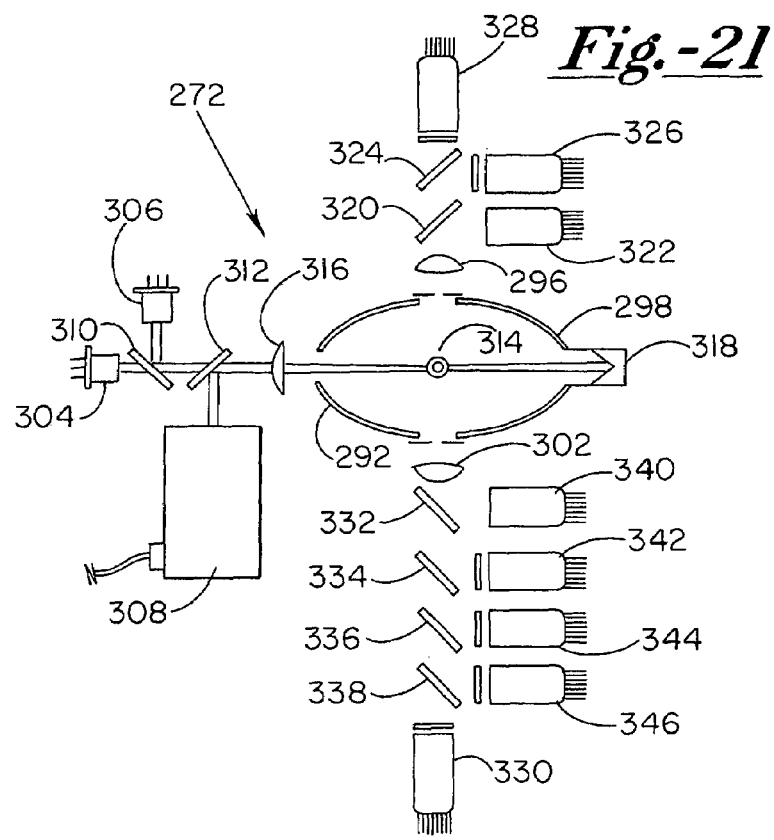
Figure 22:
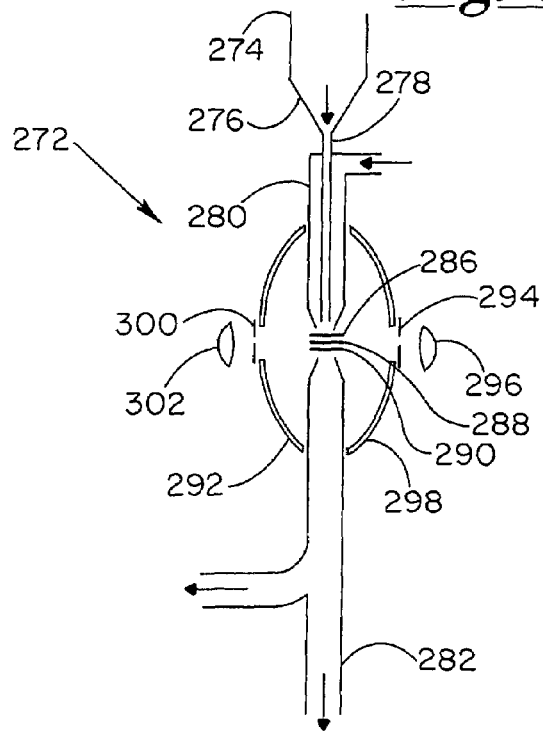
Figure 23:
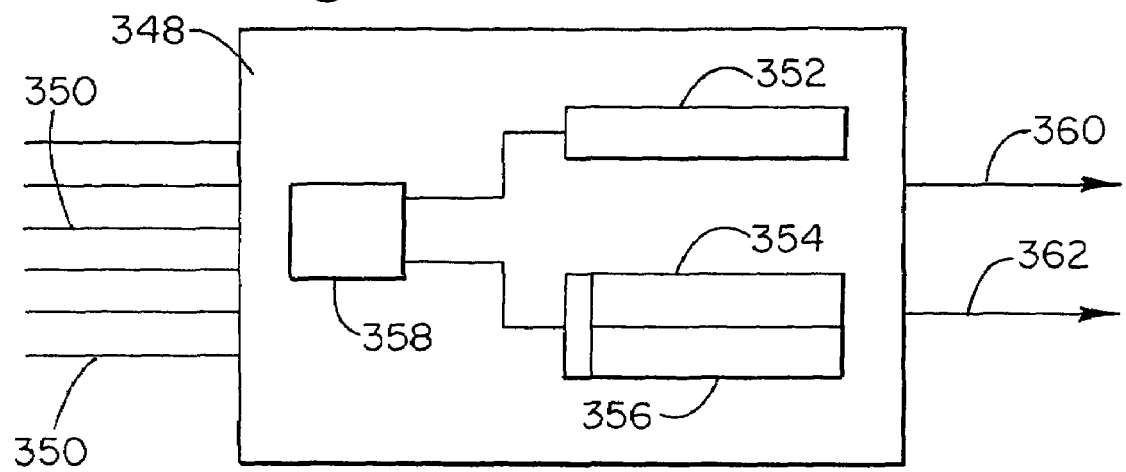
Figure 24:
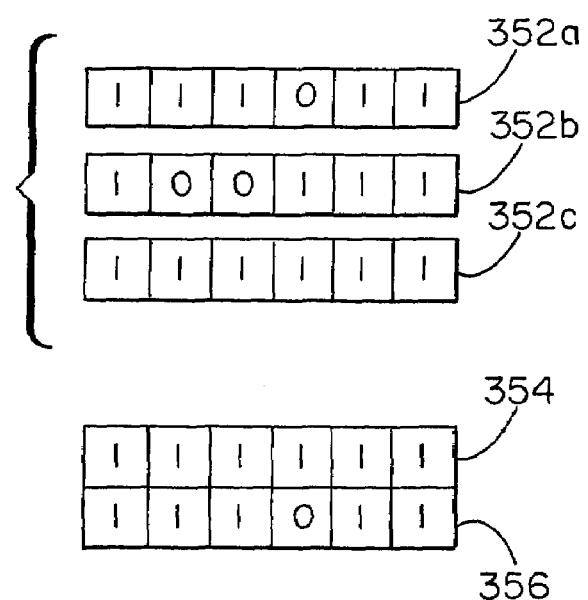

FIG. 5 schematically illustrates a system in which lasers of two different wavelengths are employed in conjunction with two detectors;

FIG. 6 is a flow chart illustrating use of the system in FIG. 5;

FIG. 7 illustrates a system employing a single detector with feedback to two lasers of different wavelengths;

FIG. 8 is a flow chart illustrating use of the system shown in FIG. 7;

FIG. 9 is a schematic view of a system similar to that shown in FIG. 7 and further incorporating color discrimination;

FIG. 10 is a flow chart illustrating use of the system in FIG. 9;

FIG. 11 illustrates a system employing two lasers of different wavelengths in conjunction with two detectors, each of which provides feedback to the lasers;

FIG. 12 illustrates a system in which one of two detectors provides feedback to lasers with different wavelengths;

FIG. 13 is a flow chart illustrating use of the systems in FIGS. 11 and 12;

FIG. 14 illustrates a system similar to that in FIG. 11, further employing a third detector;

FIG. 15 is a flow chart illustrating operation of the system in FIG. 14;

FIG. 16 illustrates a system employing a single detector in conjunction with two different violet or UV lasers;

FIG. 17 illustrates a system combining aerodynamic sizing, fluorescence sensing, and downstream mass spectrometry;

FIG. 18 is a more detailed view of a particle characterization device employing two different lasers and three detectors;

FIG. 19 schematically illustrates a detector with several different channels or photodetector elements;

FIG. 20 schematically illustrates a system featuring either excitation laser control, or detector gain control, for enhancing the range of detector sensitivity;

FIG. 21 illustrates a particle characterizing system incorporating multiple photodetectors and color discrimination;

FIG. 22 is a side view of the system in FIG. 21;

FIG. 23 is a schematic view of a microprocessor component of the system in FIGS. 21 and 22;

FIG. 24 illustrates several memory registers of the microprocessor; and

Figure 25:
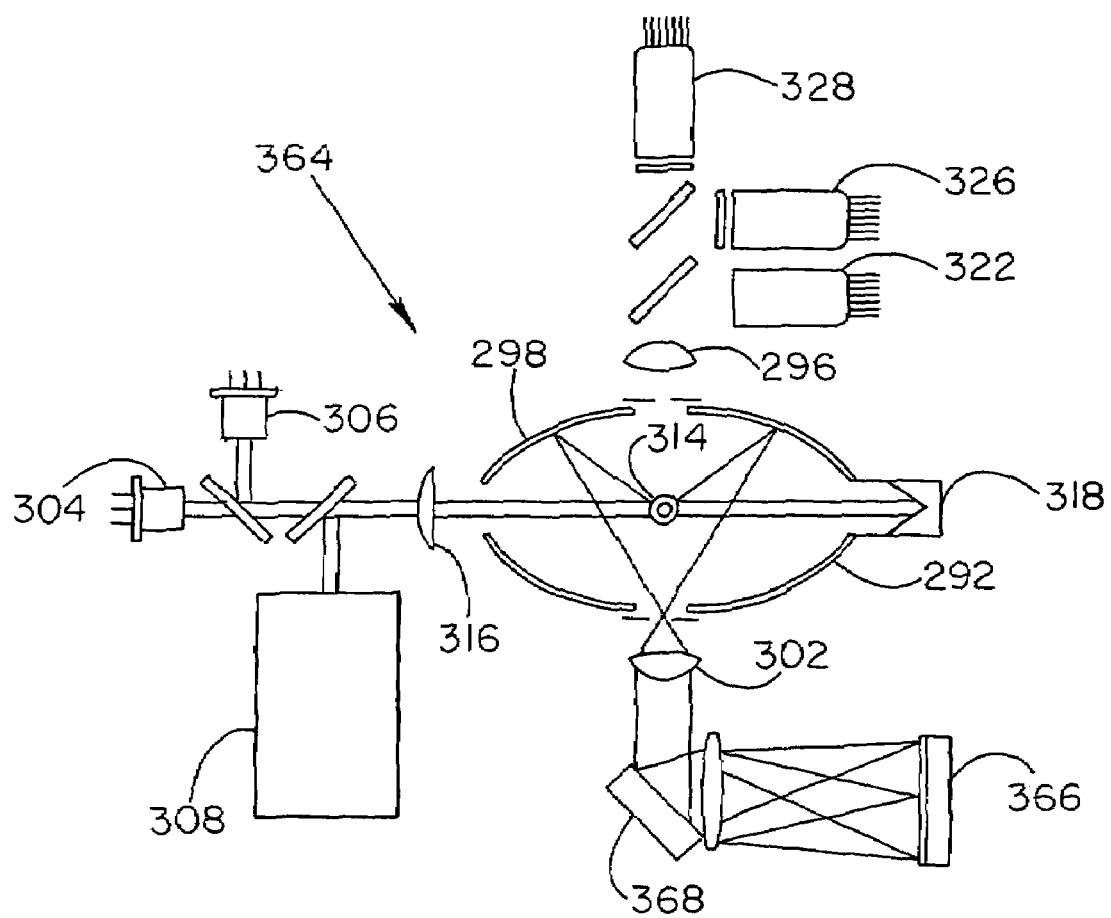

FIG. 25 is a top view of an alternative system incorporating a multi-channel detector in associating with a spectrometer grating.

DETAILED DESCRIPTION OF THE PREFERRED EMBODIMENTS

Figure 1:
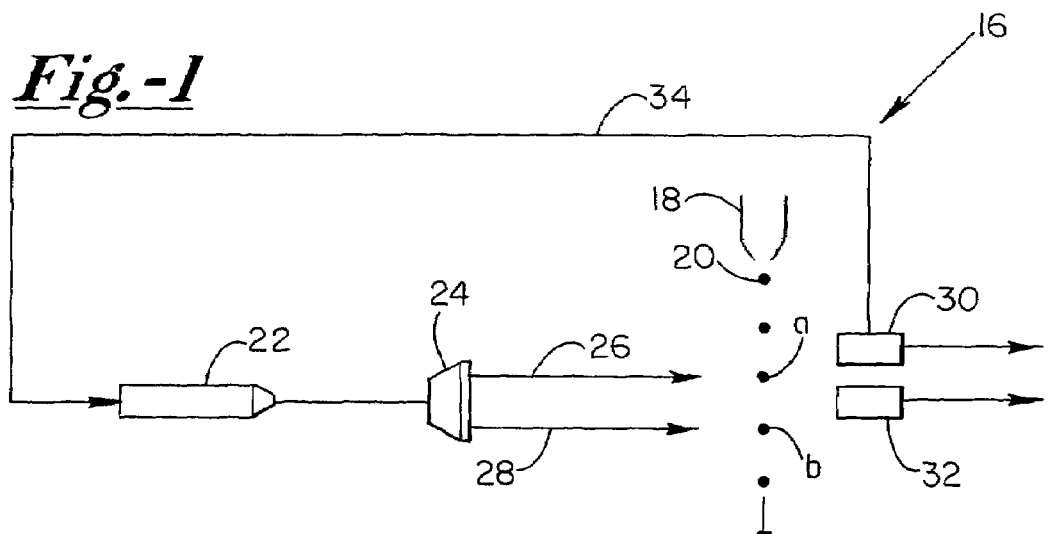
FIG. 1 is a schematic view of a particle characterizing system employing two beams of the same wavelength in association with upstream and downstream detectors.

Turning to the drawings, FIG. 1 shows an electro-optical system 16 for characterizing particles or other aerosol components (such as droplets) carried in a gas stream. The aerosol is drawn from a nozzle 18 into a partially evacuated chamber, for aerodynamic sizing and exposure to excitation energy which, depending on the nature of the particles, can cause the particles to emit energy in response to the exposure, i.e. to fluoresce. Particles 20 are carried serially, downwardly as viewed in the figure. The system employs a single diode laser 22 for generating a laser beam in the violet range, more particularly at a wavelength of 405 nm. Other violet wavelengths can be employed, as well as wavelengths in the ultraviolet (UV) range, e.g. about 200–400 nm. Beam splitting optics 24 are employed to split the laser beam into a pair of beams 26 and 28, both of which intersect the aerosol stream. Laser 22 is operated to provide beams 26 and 28 in the continuous wave (CW) mode.

As each of particles 20 reaches a point "a" along the particle stream to encounter beam 26, it scatters light which is detected by a detector 30, e.g. a photomultiplier tube or an avalanche photodetector. Each particle 20 that further is fluorescent, also emits fluorescent energy in response to exposure to the 405 nm wavelength at this point. Accordingly, in such case detector 30 receives the fluorescent energy as well as the scattered energy. However, because the intensity of the scattered light is considerably greater than that of the fluorescent energy, the response of detector 30 is determined essentially by the scattered light. Proceeding onward to point "b" along the stream, each particle encounters beam 28, and as a result emits fluorescent energy, typically at a wavelength longer than that of the excitation energy. The fluorescent energy is sensed by a detector 32. The particle also scatters energy at the 405 nm wavelength, which again is sensed by detector 30, and may also be sensed by detector 32, depending on the detector's sensitivity range.

The duration between the sensing of elastic scatter by detector 30 when each particle reaches point "a" and the sensing of elastic scatter by detector 30 when that particle reaches point "b," provides the time of flight value used to aerodynamically size the particle. Although sensing of the fluorescent emission at detector 32 could be used in aerodynamic sizing, the higher amplitude signal resulting from scattered light is preferred. The fluorescence detector output is used to characterize the nature of the particle, e.g. by identifying a biological constituent.

Given that each of detectors 30 and 32 is exposed simultaneously to elastic scatter and fluorescence, it is preferable to select a detector 32 having a tendency to reject the elastic scattering wavelength and a detector 30 having a tendency to reject the fluorescence wavelength, or to provide optical filtering to exclude the unwanted wavelength in each case.

The higher intensity of the scattered light as compared to that of the fluorescent energy results in detector outputs of different intensities. In system 16, several approaches can be used to counteract this effect and bring the detector outputs into a closer balance. The first approach involves configuring beam splitting optics to provide an unbalanced output, e.g. twenty percent of the energy to beam 26 and eighty percent of the energy to beam 28. Another approach is a selectively timed increase in the intensity of both beams. In particular, a signal path 34 couples the output of elastic scatter detector 30 to a control circuit governing laser 22, to temporarily boost laser power in response to sensing scattered light.

Preferably, the two approaches are combined. For example, laser 22 can have a baseline output of 5 mW, split to provide beam 26 at 1 mW and trailing beam 28 at 4 mW. Further, in response to the scattered light sensed at detector 30 as a particle intersects beam 26, the power to laser 22 is increased to 10 mW, with the result that beam 28 is provided at 8 mW.

Figure 2:
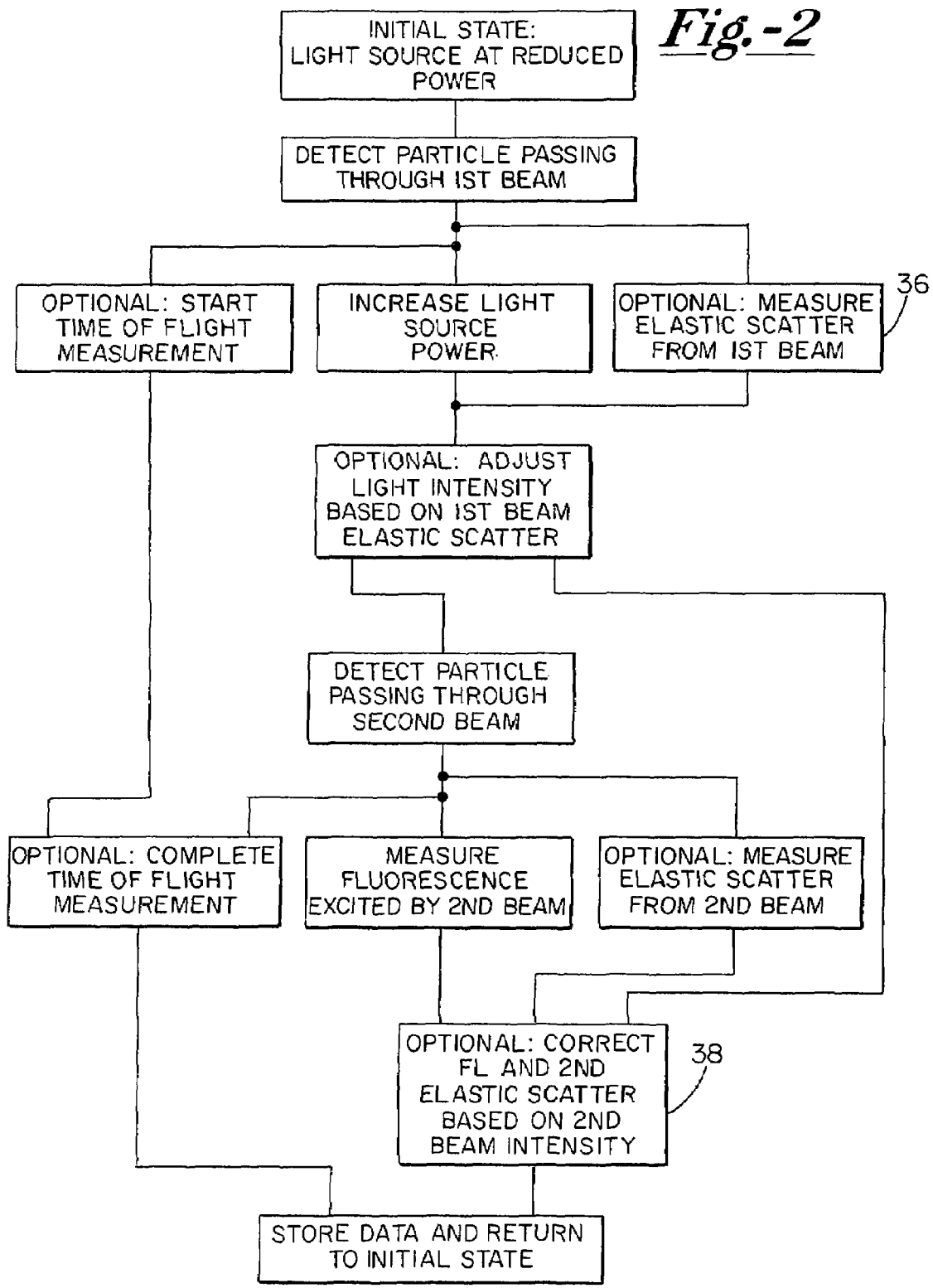
FIG. 2 is a flow chart illustrating use of the system in FIG. 1.

The flowchart of FIG. 2 illustrates the use of system 16 for particle sizing and fluorescence detection. As pointed out at 36, detector 32 optionally is used to measure scattered light as well as fluorescent energy. To this end, detector 32 includes separate portions or regions sensitive to the scattered wavelength and the fluorescent wavelength, respectively. Further, as indicated at 38, the output of detector 32, when enhanced to compensate for the lower fluorescence intensities, is corrected in conjunction with obtaining any readings based on intensity, e.g. size information to augment the aerodynamic sizing.

Figure 3:
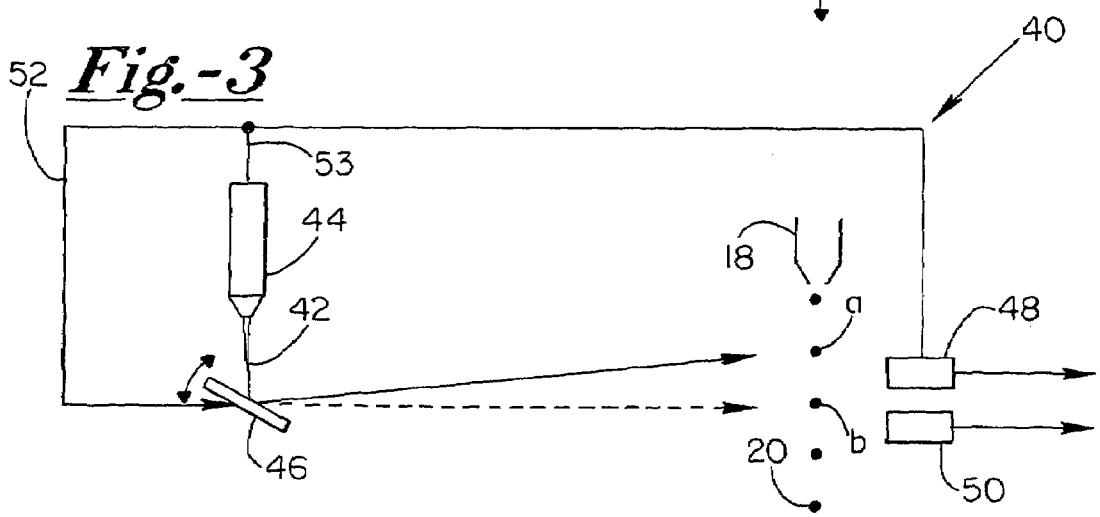
FIG. 3 illustrates an alternative particle characterization system employing a single, steerable laser beam.

FIG. 3 illustrates an alternative single-laser system 40 in which particles 20 or other components of an aerosol stream are directed in series past a single beam 42 generated by a diode laser 44. A beam steering device 46 along the beam path is controllable to alternatively position beam 42 to intersect the aerosol stream at an upstream point "a" and a downstream point "b." A detector 48 responds to light scattered by each particle as it reaches point "a." A detector 50 responds to fluorescent energy emitted by each particle in response to its exposure to violet or UV energy at point "b."

Beam steering component 46 can be a Bragg cell, a Pockels cell or a Kerr cell, the latter two being used in conjunction with polarization dependent beam positioning. In each case beam 42, initially directed through point "a," is steered to cross the aerosol stream at point "b" in response to the sensing of scattered light at detector 48. More particularly, a detector 48 output indicating receipt of scattered light is transmitted via a signal path 52 to a controller for beam steering component 46.

As indicated at 53, the output of detector 48 simultaneously is provided to laser 44 to effect a temporary increase in power to the laser, thus to compensate for the difference in detector 48 and 50 output intensities, as discussed in connection with system 16.

Figure 4:
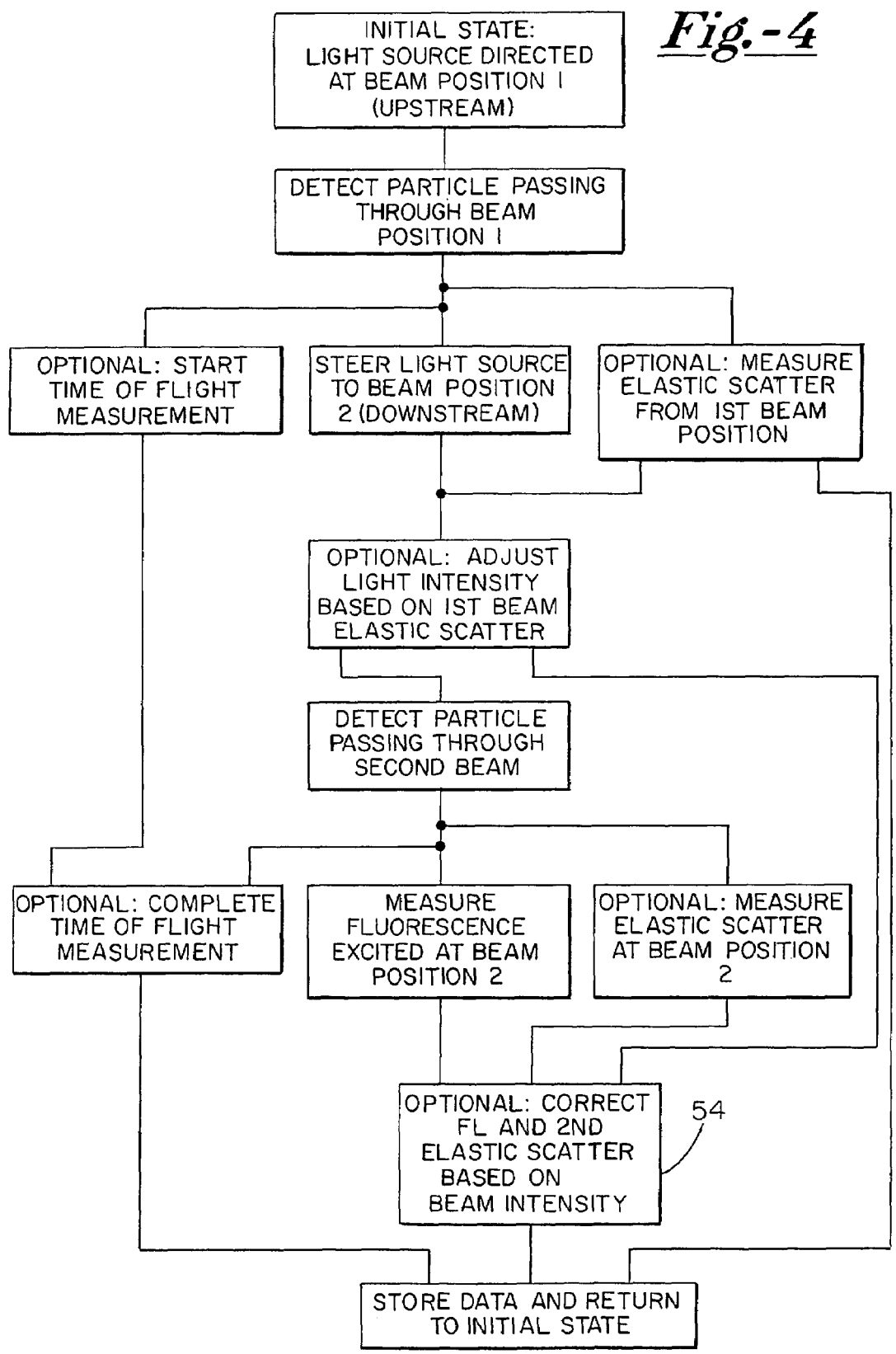
FIG. 4 is a flow chart illustrating use of the system in FIG. 3.

As seen from the accompanying flowchart (FIG. 4), operation of system 40 is similar to the operation of system 16. Again, downstream detector 50 can be used to measure scattered light as well as fluorescent energy, with that detector including different components responsive to the different wavelengths involved. As indicated at 54, when the intensity of laser 44 is temporarily increased, the resulting measurements at detector 50, whether based on fluorescence alone or also including scattered light, are corrected accordingly.

As a further feature in systems 16, 40, or the other systems to be described, each detector adapted to respond to fluorescent energy can consist of several components sensitive to different wavelengths of fluorescent energy.

FIG. 5 illustrates a system 56 in which a diode laser 58 generates a CW beam 60 of red or near infrared energy, e.g. a 680 nm wavelength, with a diode laser 62 emitting a downstream violet or UV beam 64. An upstream detector 66 generates an output in response to receiving scattered light when one of particles 20 encounters beam 60 along the aerosol stream. The output is used to initiate a time-of-flight measurement, and as indicated by the signal path 68 with an input to laser 62, also is used to activate the normally inactive laser in response to receiving the scattered light. Laser 62 can be activated immediately, or a delay can be interposed as indicated at 67 to time activation of laser 62 at or just ahead of the particle's expected arrival at point "b" along the aerosol stream. Accordingly, laser 62 is not continuously maintained in the CW mode. Alternatively, laser 62 can be maintained in a CW mode at low power, then boosted temporarily to a higher power responsive to a sensing of scattered light at detector 66.

Thus activated or powered up, laser beam 64 irradiates the earlier sensed particle as it reaches point "b," causing the particle to emit fluorescent radiation sensed by a downstream detector 70.

In an alternative arrangement of system 56, laser 58 can be replaced with a violet or UV laser, preferably emitting a wavelength different than that of laser 62. This provides the option of sensing fluorescence with upstream detector 66, and sensing scattered energy at downstream detector 70. According to a further option, scattered light and fluorescent energy can be sensed at both upstream and downstream locations.

Regardless of the option, energy sensed at the beginning of each time-of-flight measurement is of a different wavelength than the energy sensed at the end of the measurement, providing a color discrimination that positively identifies the starting and ending timing signals.

FIG. 6 is a flowchart illustrating the options available in using system 56.

FIG. 7 shows a system 72 similar to system 56, in that a diode laser 74 generates an upstream beam 76 in a controlled CW mode. A normally inactive diode laser 78 generates a downstream beam 80 when activated by the sensing of scattered light. Preferably beam 80 has a shorter wavelength than beam 76. A single photodetector 82 responds to light scattered by a particle 20 as it crosses beam 76 at point "a," and further responds to fluorescent energy emitted by particle 20 immediately after its irradiation by beam 80 at point "b."

The output of detector 82 is provided via a signal path 84 as an input to activate or power up laser 78 in response to receipt of scattered light. As indicated at 86, the detector output also is provided as an input to laser 74. This switches laser 74 off temporarily, in particular until after the time the particle is expected to intersect beam 80. Thus, longer wavelength beam 76 is not present during the period that the particle may emit fluorescent energy in response to its irradiation by shorter wavelength beam 80.

The flowchart of FIG. 8 illustrates the operation of system 72.

FIG. 9 shows a single detector system 88 including a diode laser 90 generating an upstream beam 92 having a longer wavelength, e.g. red or infrared, in a CW mode. A diode laser 94 is used to generate a downstream beam 96 having a shorter wavelength, preferably in the violet or UV range. A single detector 98 is positioned to receive light scattered by each particle as it encounters beam 92 at point "a" along the aerosol stream, and also is positioned to receive fluorescent energy emitted by the particle from point "b" responsive to its irradiation by beam 96. As indicated at 100 and 102, the output of detector 98 is provided as an input to diode laser 90 and to diode laser 94. Responsive to receiving scattered energy from the particle at point "a," detector 98 switches diode laser 90 off and activates diode laser 94 to illuminate the region of point "b." Detector 98 preferably is sensitive to longer wavelengths/lower frequencies, and thus excludes elastic scatter of downstream laser beam 96, which has a higher frequency/shorter wavelength than either beam 92 or the fluorescent energy stimulated by exposure to beam 96. Alternatively, discrimination is achieved with the aid of a filter, grating or prism 103.

System 88 is capable of measuring aerodynamic size with color discrimination to unambiguously identify time-of-flight starting and ending times, for all particles that emit fluorescent energy of sufficient amplitude in response to irradiation by beam 96.

FIG. 10 is a flowchart illustrating the operation of system 88.

FIG. 11 illustrates a system 104 employing two detectors to facilitate time-of-flight measurements based on scattered light. Like system 88, system 104 uses a diode laser 106 to generate an upstream beam 108 in a CW mode, preferably a red or near infrared wavelength. A diode laser 110 generates a downstream laser beam 112 at a violet or UV wavelength. An upstream detector 114, sensitive to longer wavelengths, is responsive to light scattered by a particle 20 when the particle crosses beam 108. Detector 114 also responds to fluorescent energy emitted by the particle in response to irradiation by the violet or UV energy as it crosses beam 112.

A downstream detector 116 is sensitive to the violet or UV energy scattered by the particle as it crosses downstream beam 112. Preferably, downstream detector 116 is not sensitive to coherent energy scatter from upstream beam 108. If desired, detector 116 also may be insensitive to the wavelength of the fluorescent emission. This additional insensitivity is not as important, however, due to the higher intensity of the scattered energy as compared to the fluorescent energy.

A signal path 118 provides the output of upstream detector 114 as an input to diode lasers 106 and 110. Likewise, a signal path 120 provides the output of downstream detector 116 to both lasers. Accordingly, responsive to the detection of scattered coherent energy from the upstream beam, laser 106 is switched off and laser 110 is switched on, either simultaneously or after a predetermined delay corresponding to the shortest expected time-of-flight from point "a" to point "b."

An advantage of system 104 as compared to system 88 in FIG. 9 is that scattered coherent energy is used to identify both the beginning and ending of the time-of-flight measurement. As a result, particles can be aerodynamically sized, regardless of whether they are capable of fluorescing in response to irradiation by the downstream laser beam. System 104 retains the advantage of color discrimination to identify with certainty the beginning and ending of each time-of-flight measurement.

The laser inputs from downstream detector 116 switch laser 106 back on and switch laser 110 off, responsive to sensing scattered energy from downstream beam 112. As an option, laser 106 can be switched on and laser 110 can be switched off in response to the detection of fluorescent energy by upstream detector 114. More particularly, when beam 112 causes a particle at point "b" to fluoresce, detector 114 senses the fluorescent energy and provides the appropriate signal to lasers 106 and 110 via path 118. As a further option, the upstream laser can be turned on and the downstream laser turned off after a predetermined delay, eliminating the need for this second control input from either detector.

To facilitate a placement of upstream detector 114 to receive both energy scattered by a particle crossing beam 108 and energy emitted by the particle when crossing downstream beam 112, the laser beams (i.e., points "a" and "b") are preferably separated by a distance of at most about 0.5 mm.

System 104 (FIG. 11) can be configured with a single primary optical element to collect scattered energy from both lasers, and fluorescent energy emitted by the particles crossing beam 112. In this event, collected light is color separated into a longer wavelength band transmitted to detector 114, and a shorter wavelength band transmitted to detector 116. Alternatively, two primary light collection optical elements are provided, one for each detector.

The elastic scatter reaching upstream detector 114 is likely to have a significantly higher amplitude (e.g. by an order of magnitude) than the fluorescent energy reaching that detector. To compensate for this difference, separate channels 122 and 124 can be coupled to provide different levels of amplification or gain to the detector output signal. Gain switching can be employed as an alternative. A disadvantage of this arrangement is the potential for the scattered energy from upstream beam 108 to produce a signal in upstream detector 114 large enough to cause saturation or otherwise interfere with detection of the subsequent fluorescence signal.

FIG. 12 illustrates a system 126 similar to system 104, with an upstream laser 128 generating a CW beam 130 of red or near infrared energy, and a laser 132 generating a downstream beam 134 in the violet or UV wavelength range. The system includes two detectors: An upstream detector 136 configured to detect energy from beam 130 scattered by a particle passing point "a", and scattered energy from beam 134 when the particle passes point "b." Thus, detector 136 provides both the beginning and ending time-of-flight signals. Detector 136 also can be used to measure the intensity of the scattered energy from both beams.

A downstream detector 138 is configured to detect fluorescence emitted by particles in response to irradiation by beam 134 as they pass point "b." In this arrangement, fluorescence detector 138 preferably is configured to be sensitive only to a band of wavelengths between those of lasers 128 and 132.

Alternatively, if the wavelengths of lasers 128 and 132 are sufficiently close to one another, for example if laser 128 has a wavelength in the violet rather than the red or near infrared range, the fluorescent energy has a wavelength longer than that of either beam. In this event downstream detector 138 is configured to be sensitive to wavelengths longer than those of the lasers.

A signal path 140 provides the detector 136 signal as an input to lasers 128 and 132, to facilitate using this signal to switch off laser 128 and activate laser 132 either simultaneously or after a predetermined delay. If desired, a signal path also can be used to provide, to both lasers, the detector 138 signal responsive to fluorescent energy emitted due to downstream beam 134. This later input activates laser 128 and switches laser 132 off, resetting the system for sensing the next particle.

FIG. 13 is a flowchart illustrating the operation of systems 104 and 126.

FIG. 14 shows a system 142 including a laser diode 144 for generating an upstream beam 146 in a CW mode, and a diode laser 148 for generating a downstream laser beam 150, normally inactive and triggered by sensing scattered light from the upstream beam. Beam 146 is generated in the red or near infrared range, while beam 150 is generated in the violet or UV range.

System 142 includes three detectors: A detector 152 responsive to light scattered from upstream beam 146, a detector 154 responsive to light scattered from downstream beam 150, and a detector 156 for sensing fluorescent energy emitted by particles responsive to irradiation by downstream beam 150. As each of the detectors is associated with only one of the lasers, there s no need to locate beams 146 and 150 sufficiently close to one another so that the same detector can receive scattered or emitted energy due to both beams. Aerodynamic sizing is based on scattered energy alone, with color discrimination to positively identify the starting and ending signals of the time-of-flight measurement.

A signal path 158 provides the detector 152 output to lasers 144 and 148, deactivating beam 146 and activating beam 150 in response to scattering from beam 146 as previously explained. Similarly, a signal path 159 provides the detector 154 output to the lasers to reset the system.

In an alternative configuration of system 142, both of diode lasers 144 and 148 generate beams having wavelengths in the violet or ultraviolet range, and are used to stimulate fluorescent emissions by the particles. Thus, depending on their make-up, particles may emit fluorescent energy at two different wavelengths as they proceed through the system. This increases the system capacity to recognize additional constituents, for a more thorough analysis of the particles.

FIG. 15 is a flow chart illustrating the operation of system 142.

FIG. 16 illustrates a single-detector system similar 160 to system 72 (FIG. 7). Diode lasers 162 and 164 respectively generate and upstream beam 166 and a higher frequency downstream beam 168. Both beams have wavelengths in either the violet or ultraviolet range, and are used to stimulate fluorescent emissions, so that each particle fluoresces at point "a" and point "b" along the aerosol path. A single detector 170 is configured to respond to both of the expected fluorescent wavelengths.

A signal path 172 provides the detector output to laser 162 and laser 164. The detector output in response to fluorescence emitted at point "a" is used to switch off upstream beam 166 and activate downstream beam 168. If desired, the detector output responsive to fluorescent energy emitted at point "b" can be provided to the lasers to reset the system.

In system 160, beams 166 and 168 cause particles of a certain make-up to emit fluorescent energy at two different wavelengths, as in system 142 when in the alternative configuration discussed above. Aerodynamic particle sizing is based on the scattered light from beams 166 and 168, providing different wavelengths to positively identify the starting and ending signals in the time of flight measurement.

In a variant of system 160, upstream beam 166 can be provided with a wavelength shorter than that of downstream beam 168, although both remain in the violet or UV range. According to a further variant of this system, the single detector 170 can be replaced with a pair of detectors, one responsive to each of the anticipated fluorescent wavelengths.

FIG. 17 illustrates a system 173 for aerodynamically sizing particles, irradiating the particles to stimulate fluorescence and detecting the fluorescence, then subjecting the particles to further analysis in a mass spectrometer. A diode pumped, solid state laser 174 is used to generate an upstream laser beam 176 in a CW mode with a visible wavelength, e.g. 532 nm. A laser 178 is used to generate a downstream laser beam 180, preferably in the violet or UV range, e.g. 405 nm, 355 nm or 266 nm. An upstream detector 182 is sensitive to light scattered by particles encountering the upstream beam, while a downstream detector 184 is sensitive to light scattered by particles encountering the downstream laser beam. Downstream detector 184 further is configured for sensitivity to fluorescent energy emitted by particles in response to their irradiation by the downstream laser beam. Upstream and downstream ellipsoidal mirrors 186 and 188 are positioned along the aerosol path where the particles intersect the upstream and downstream beams, respectively. The mirrors enhance sensitivity by reflecting scattered or irradiated energy toward one of each mirror's foci, as further explained in the aforementioned U.S. Pat. No. 5,999,250.

As in certain previous embodiments, upstream detector 182 provides its output to diode lasers 174 and 178 turning the upstream beam off and activating the downstream beam in response to sensing a particle at the upstream beam.

In an alternative approach, diode laser 174 generates the upstream laser beam at a wavelength in the UV or violet range, capable of inducing fluorescence in the particles. Then, either of detectors 182 and 184, or both detectors if desired, can be configured for sensitivity to fluorescent energy. The latter case facilitates sensing for two different fluorescent wavelengths, assuming the upstream and downstream beams have different wavelengths. According to a further option for this approach, detectors 182 and 184 are sensitive only to the fluorescent energy, whereby only particles that emit fluorescent energy are aerodynamically sized.

After aerodynamic sizing, the particles proceed to a time-of-flight mass spectrometer 190. Spectrometer 190 includes a laser 192 generating a laser beam 194 in the UV range, e.g. 266 nm, directed to intersect the aerosol stream. Beam 194 is generated at a considerably higher power level than the preceding beams, e.g. over one millijoule, sufficient to desorb and ionize each particle irradiated by the beam.

Source plates 196 near the intersection of beam 194 and the particle stream create an electric field that accelerates positive ions to the left as viewed in FIG. 18, and accelerates negative ions to the right. Reflectrons or ion mirrors at 198 and 200 direct their associated ions back toward the center of spectrometer 190, where the ions encounter respective microchannel plate ion detectors 202 and 204. Each of the ion detectors generates time-of-flight readings when encountered by its associated ions. Ions are distinguishable from one another based on different mass-to-charge (m/z) ratios, which lead to different rates of acceleration due to the electric field and different time-of-flight measurements, resulting in the capacity to distinguish among ions according to differing times of flight.

Time-of-flight mass spectrometry requires a near vacuum. To this end, aerosol entering a nozzle 206 at or near atmospheric pressure is reduced to a pressure of about 2 Torr by the time it exits the nozzle. Two further pumping stations reduce the pressure to $10^{-4}$ Torr by the time the aerosol reaches the particle sizing region, where the particles pass through upstream and downstream beams 176 and 180. Smaller particles are accelerated to higher terminal velocities, resulting in shorter times-of-flight between the two laser beams. For each particle, the time between the output signals of detectors 182 and 184 indicates a diameter.

The particles proceed through an orifice 208 into mass spectrometer 190, where pressure is maintained at about $2 \times 10^{-7}$ Torr. The transit time of each particle from upstream beam 176 to downstream beam 180 is used to control the firing of ultraviolet laser 192. Laser beam 194 desorbs and ionizes the particle, and the resulting ions are accelerated and produce varying times of flight as described above.

Any of the previously discussed particle characterizing systems can be used in conjunction with a mass spectrometer, to recognize fluorescence and aerodynamically size the particles as they approach the mass spectrometer. The aerodynamic sizing information is used to time the firing of the ionizing laser. The particle characterizing capability can be used to discriminate among the aerosol particles, for example by causing the ionizing laser to fire only in response to sensing each particle that emits fluorescent energy, only in response to particles that emit fluorescent energy at a given wavelength or wavelength range, or only in response to particles that do not emit fluorescent energy when exposed to the excitation wavelength.

When required to respond to the sensing of each and every particle, the ionizing laser limits the speed of a particle characterizing system, due to the time required between successive activations of the laser. However, when the ionizing laser is selectively controlled to fire only in response to a subset of the particles, e.g. those that emit fluorescent energy, this limitation upon system speed is counteracted.

Alternative ionizing and ion detection instruments may be used in lieu of the time-of-flight mass spectrometer.

FIG. 18 illustrates in more detail a 2-laser, 3-detector arrangement. Diode lasers 210 and 212 generate respective beams 214 and 216 that are initially orthogonal, then encounter a dichroic separator 218, after which the laser beams are parallel and directed toward the aerosol path, which in FIG. 18 is perpendicular to the plane of the drawing. A first ellipsoidal reflector 220, positioned with one of its foci along the aerosol stream, reflects scattered or emitted energy toward an upstream detector 222 positioned at the other focal point. In similar fashion, a second ellipsoidal reflector 224 is positioned with one focal point along the aerosol stream, and the other focal point centered on an aperture 226 leading through a lens 228 to a second dichroic separator 230, then to a second detector 232. A third detector 234 receives another portion of the energy from dichroic separator 230. Detectors 232 and 234 and separator 230 can be configured, for example, to distinguish between scatter from the second laser and fluorescent energy emitted as a result of a particle's exposure to the second laser beam.

As an additional feature in any of the particle characterizing systems discussed above, it is possible to use gratings, filter arrays, and other color discrimination devices to separate fluorescent energy into distinct color bands. FIG. 19 shows a detector 236 having separate photodetector elements 238, 240 and 242, each sensitive to a different bandwidth within the fluorescent range. The detector receives fluorescent energy 244 emitted by a particle 20 in response to its irradiation by coherent energy in the violet or UV range. The photodetector elements provide respective outputs 246, 248 and 250, corresponding to the different frequencies of fluorescent energy sensed.

In connection with any one of the above systems, there may be a need for detecting fluorescent energy over a wider than usual range of signal amplitudes. In such cases, detectors with sufficient sensitivity to respond to the lower amplitude signals might be saturated by the high amplitude fluorescent signals. There are several ways to counteract this problem. For example, when elastic scattering detection precedes fluorescent energy detection, the amplitude of the detected scattered light can be used to control the intensity of the excitation laser, or to control the gain in the fluorescence detector. Alternatively, a wider dynamic range can be achieved while minimizing or avoiding the risk of saturation, by using a fluorescence detector output to control the amplitude of laser irradiation of the fluorescent particle. FIG. 20 shows a diode laser 252 generating a beam 254 in the violet or UV range, to irradiate a particle 20. The resulting fluorescent emission 256 is sensed by a detector 258. A laser control circuit 260 provides power to laser 252 according to a fast ramp function in which power to the laser, and the resulting amplitude of beam 254, increase rapidly and substantially linearly.

The output of fluorescence detector 258 is provided via a signal path 262 as an input to control circuit 260. As indicated at 264, a reference signal also is provided to the control circuit. The reference signal is an amplitude threshold, corresponding to an upper limit for the intensity of fluorescent energy beam 256 at detector 258. The upper limit is set below an amplitude that might saturate the detector.

The amplitude of the detector 258 output varies with the intensity of beam 256 at the detector. So long as the amplitude remains below that of reference signal 264, power to the laser can follow the ramp function, up to a predetermined maximum operating level selected with respect to the laser involved. However, if the detector 258 output amplitude reaches or exceeds the reference level, control circuit 260 is caused to clamp the ramp function, so that power to laser 252 is stabilized at less than the predetermined maximum operating level.

As a further option, an optical separating device 266 can be used to divert a fraction of beam 254 to a detector 268, and the output of detector 268 provided as another input to control circuit 260 via a signal path 270. In conjunction with this input, reference 264 or a separate reference signal is set at a level corresponding to a selected maximum amplitude for beam 254.

FIGS. 21 and 22 illustrate a multiple-laser, multiple-detector particle characterizing system 272 employing three different wavelengths capable of inducing responsive fluorescent emissions in biological particles. Turning first to FIG. 22, the system includes an aerosol inlet 274 to an aerosol concentrator 276 configured in cooperation with a pump (not shown) to draw an aerosol at a rate of about 500 1 pm, thus to move a majority of aerosol particles having a diameter greater than 1 micron, serially through an internal conduit 278 toward the optical chamber. Filtered sheath air is provided through an exterior conduit 280, to confine the aerosol and keep it centered on the predetermined path. Centering enhances readings by maintaining each particle substantially centered within each of the laser beams. Confining the aerosol prevents the particles from recirculating within, and potentially contaminating, the optical chamber. Beyond the lasers, the aerosol is drawn out of the optical chamber through an exit conduit 282. In the optical chamber, particles pass laser beams 286, 288 and 290 in succession. An ellipsoidal reflector 292 collects radiant energy (both scattered light and fluorescent emissions) due to lasers 286 and 288, and directs the energy through an aperture 294 to an optical collector (lens) 296. In similar fashion, an ellipsoidal reflector 298 collects energy resulting from laser beam 290 and directs it through an aperture 300 to an optical collector 302.

As seen in FIG. 21, the source of laser beam 286 is a laser diode 304, operated in the CW mode to generate the beam at a wavelength of 405 nm. The laser diode 306 generates beam 288 in the CW mode, at a wavelength of 370 nm. A laser 308 generates beam 290 in a pulsed mode, at a wavelength of 266 nm. Thus, the excitation wavelengths generally are within the range of 260–420 nm.

Laser beams 286 and 288 initially are orthogonal, then directed in parallel by a dichroic element 310. Similarly, a dichroic element 312 aligns laser beam 290 with beams 286 and 288. The beams are parallel, but separated from one another in the direction of aerosol path 314 as best seen in FIG. 22. A convex lens 316 focuses the beams, thus to provide in each case a narrow beam waist coincident with the aerosol path. A beam stop 318 is located across from lens 316, beyond the ellipsoidal reflectors.

Each of beams 286, 288 and 290 is capable of being scattered by the particles as they pass through the optical chamber. Each beam further is selected to trigger a responsive emission, more particularly a fluorescent energy emission, from the irradiated particles depending on particle composition.

As previously noted, ellipsoidal reflector 292 collects radiant energy scattered and emitted due to laser beams 286 and 288, directing this energy to optical collector 296. Beyond the optical collector, a dichroic filter 320 separates part of the energy by wavelength, directing it horizontally as viewed in FIG. 21 to a detector 322 (a photomultiplier) configured to sense scattered light. The remainder of the energy proceeds to a dichroic filter 324, where another wavelength segment of the energy is directed to a fluorescence detector 326. The remainder of the energy proceeds to a fluorescence detector 328.

Similarly, energy collected by ellipsoidal reflector 298 and directed through optical collector 302 proceeds toward a fluorescence detector 330, vertically as viewed in FIG. 21. Dichroic filters 332, 334, 336 and 338 direct wavelength segments of the energy in succession to a detector 340 configured for sensing scattered energy from the pulsed laser, and successive wavelength segments to detectors 342, 344 and 346, for sensing the fluorescent energy at different wavelengths.

As seen in FIG. 23, system 272 includes a microprocessor component 348 resident in a personal computer (not shown), or alternatively configured into one or more system components. Among the inputs to the microprocessor are six inputs 350, each providing one of the outputs of the fluorescent energy detectors to the microprocessor. Microprocessor memory includes a dynamic register 352 for dynamically storing particle response patterns or profiles, and a register 354 for storing a reference profile. If desired, several reference profiles can be stored, corresponding to several different fluorescing materials, as indicated at 356 in FIG. 24.

Microprocessor 348 incorporates comparator logic 358, in the form of a computer program or embedded firmware. In connection with each sensed particle, the comparator is configured to match the contents of dynamic register 352 with each reference register, and to generate a positive or high output 360 if a match is found, or to generate a low or "null" output 362 if a match is not found. Thus, in the case of three particles with successive profiles in register 352 indicated at 352a, 352b and 352c, respectively, the microprocessor output is high with respect to profiles 352a and c, and low with respect to profile 352b. As a result, only the particles associated with profiles 352a and 352c are selected for further analysis, for example mass spectrometry as indicated in FIG. 17.

In one preferred approach, data from particles are stored in matrices based on several measured parameters, such as particle size, amplitude of fluorescent energy emitted at a first location along the path, and amplitude of fluorescent energy emitted at a second location along the path. Multiple measurements are taken, with each matrix location preferably containing the results of several measurements. For example, out of 100 particles in a sample, the size matrix might contain five particles, and the two fluorescent amplitude matrices might include 20 particles and 10 particles, respectively. The necessary memory, logic and other microprocessing functions preferably reside in a system component.

At selected time intervals, or after a selected sample size, the accumulated data are transmitted to a personal computer, or to another microprocessing environment in a system component, where a computer program is operable to compare the cumulative profiles or patterns with predetermined profiles.

Preferably the system is operable to create predetermined profiles associated with specific particle constituents. This is accomplished, for example, by testing multiple particles of a known composition, to determine a cumulative profile based on the multiple measurements obtained. If this is repeated for several constituents, the resulting set of predetermined profiles can be used in testing samples of unknown composition in order to identify the particles involved.

FIG. 25 illustrates an alternative system 364, similar to system 272 except that in connection with detection of the scattered pulsed laser energy and the corresponding fluorescent emissions, the photodetector array and dichroic filters in system 272 are replaced with a multi-channel detector 366 and a spectrometer grating 368.

In general, these systems combine aerodynamic sizing with fluorescence detection, and can further incorporate a mass spectrometer or other ionizing/ion detection instrument to more accurately characterize aerosols. Each system provides at least two laser beams, with at least one of the beams provided at an excitation frequency (or wavelength) selected to cause aerosol particles to emit fluorescent energy. While the excitation laser usually is in the violet or ultraviolet range, other wavelengths may be employed, so long as they are capable of causing a selected material to emit fluorescent energy when exposed to the excitation wavelength. Additional beams may be used, for example to allow detection of fluorescence at several different frequencies, or to more positively distinguish scattered energy, excitation energy and fluorescent energy. In addition, or alternatively, timed activation and deactivation of lasers is used to prevent the different energy wavelengths from interfering with one another, and to distinguish among these wavelengths.

What is claimed is:

1. A process for analyzing particles, including:
moving multiple particles serially along a predetermined path;
irradiating each particle with excitation energy as it traverses the path, wherein the excitation energy comprises energy at a first excitation frequency selected to cause a responsive emission depending on particle composition;
in connection with each irradiation of a particle, sensing for a responsive emission to determine an emissive response profile associated with the particle; and
selecting, for further analysis, only the particles associated with emissive response profiles that coincide with a predetermined reference profile.

2. The process of claim 1 further including:
after selecting the particles, performing the further analysis on the selected particles.

3. The process of claim 2 wherein:
the further analysis comprises irradiating each of the selected particles with ablation energy to desorb and ionize the particle.

4. The process of claim 3 wherein:
the further analysis comprises time-of-flight mass spectrometry.

5. The process of claim 1 wherein:
said irradiating of each particle includes causing a first beam of excitation energy at the first excitation frequency to intersect the predetermined path at a first location.

6. The process of claim 5 wherein:
said irradiating further includes causing a second beam of excitation frequency at a second frequency to intersect the predetermined path at a location downstream of the first location, wherein the second excitation frequency is selected to trigger a second responsive emission depending on particle composition; and
said sensing includes determining the emissive response profile based on the first and second responsive emissions.

7. The process of claim 1 wherein:
said moving of the multiple particles comprises drawing an aerosol including the particles along the predetermined path.

8. The process of claim 1 further including:
measuring the sizes of at least the selected particles, based on a characteristic selected from the group consisting of: an intensity of light scattered by each particle; and a time-of-flight for each of the particles between first and second locations along the predetermined path.

9. The process of claim 1 wherein:
said selecting includes measuring particles of a known composition to create the predetermined profile, and comparing the emissive response profiles of particles under test to the predetermined profile.

10. The process of claim 1 further including:
sensing for responsive emissions with respect to multiple particles, and using the results of the multiple sensing episodes to provide a cumulative emission response profile.

11. The process of claim 1 wherein:
the excitation energy has a wavelength within a range from about 260 to about 420 nm.

12. The process of claim 1 wherein:
said sensing for the first responsive emission consists essentially of sensing for fluorescent energy.

13. The process of claim 12 wherein:
the first emissive response includes fluorescent energy at a plurality of different wavelengths, and said sensing for the responsive emission includes using separate sensors or detecting channels to individually detect the different wavelengths.

14. The process of claim 1 wherein:
said selecting comprises using detectors sensitive only to fluorescent energy, whereby the step of selecting for further analysis is performed only on particles that emit fluorescent energy in response to said irradiating.

15. A system for analyzing particles, including:
a flow generating device for moving a particle-containing fluid along a designated path to carry the particles serially along the dedicated path;
an excitation component for providing excitation energy comprising energy at a first excitation frequency selected to cause a responsive emission depending on particle composition, and for irradiating the particles individually as they traverse the designated path;
a sensing component adapted to detect responsive emissions, operative in response to each irradiation of a particle to determine an emissive response profile associated with the particle; and a selecting component adapted to select for further analysis only the particles with associated emissive response profiles that coincide with a predetermined reference profile.

16. The system of claim 15 further including:
a particle analyzing instrument disposed along the designated path.

17. The system of claim 16 wherein:
the instrument comprises an ablation energy source adapted to desorb and ionize the selected particles.

18. The system of claim 16 wherein:
the instrument comprises a time-of-flight mass spectrometer.

19. The system of claim 15 wherein:
the fluid comprises a gas.

20. The system of claim 19 further including:
a filtered air source for providing a sheath flow to surround the gas and flow with the gas as it moves along the designated path.

21. The system of claim 15 further including:
a particle sizing component comprising a detector for measuring an intensity of coherent energy scattered by each particle.

22. The system of claim 15 further including:
a particle sizing component comprising a means for timing the travel of each particle from a first location to a second location along the designated path.

23. The system of claim 15 wherein:
the excitation component is adapted to generate a first coherent energy beam at the first excitation wavelength, and a second coherent energy beam at the second and different excitation wavelength.

24. The system of claim 23 wherein:
the sensing component comprises a first detector responsive to energy in a first emissive wavelength range, and a second detector responsive to energy in a second emissive energy wavelength range.

25. The system of claim 24 further including:
an optical element for receiving the responsive emission, and providing a first selected wavelength region of the responsive emission to the first detector and a second selected wavelength region of the responsive emission to the second detector.

26. The system of claim 15 wherein:
the selecting component includes a first data storage field for dynamically storing emissive response profiles, a second data storage field for storing the predetermined reference profile, comparator logic operably associated with the first and second data storage fields for determining whether the data contained in the first and second fields coincide, and a selector adapted to select a given particle in the event of a coincidence determination.

27. The system of claim 15 wherein:
the sensing component is adapted to measure amplitudes of the responsive emissions.

28. A process for characterizing particles with controlled coherent energy sources, including:
moving multiple particles serially along a predetermined path;
generating a first coherent energy beam using a first source operable to adjust the first beam between a first state comprising a high amplitude operating mode and a second state comprising either a low amplitude operating mode or an inactive state;
generating a second coherent energy beam using a second source operable to adjust the second beam between a first state comprising a high amplitude operating mode and a second state comprising either a low amplitude operating mode or an inactive state;
while maintaining the first beam primarily in the first state, causing the first beam to intersect the predetermined path at a first location to irradiate each particle as it travels past the first location;
causing the second beam to intersect the predetermined path at a second location downstream of the first location, whereby the second beam is positioned to irradiate each particle as it passes the second location;
with respect to each particle, detecting a first response comprising radiant energy emanating from the particle in response to irradiation by the first beam; and
responsive to detecting the first response, and before the particle reaches the second location, operating the first source to switch the first beam from the first state to the second state.

29. The process of claim 28 further including:
maintaining the second beam primarily in the second state, and further responsive to detecting the first response, operating the second source to switch the second beam from the second state to the first state.

30. The process of claim 29 wherein:
said operating the first and second sources is performed after a predetermined delay following detection of the first response.

31. The process of claim 29 further including:
after said operating the first and second sources, further operating the first and second sources to reset the first beam to the first state and reset the second beam to the second state.

32. The process of claim 29 further including:
detecting a second response comprising radiant energy emanating from the particle in response to the irradiation by the second beam; and
responsive to detecting the second response, operating the first source to reset the first beam from the second state to the first state.

33. The process of claim 32 further including:
operating the second source to reset the second beam to the second state, responsive to detecting the second response.

34. The process of claim 33 wherein:
said resetting of the first and second beams is performed substantially simultaneously with detecting the second response.

35. The process of claim 32 wherein:
detecting the second response consists essentially of one of the following:
(i) detecting energy scattered by the particle when at the second location; and (ii) detecting fluorescent energy emitted by the particle when at the second location.

36. The process of claim 32 wherein:
detecting the first and second responses is accomplished with a single detector.

37. The process of claim 32 wherein:
the second response includes a scattered energy component and a fluorescent energy component, and detecting the first response and the second response comprises using a first sensor to detect energy scattered by the particle at the first and second locations, and using a second sensor to detect the fluorescent energy component.

38. The process of claim 28 further including:
sizing the particle, based either upon an amplitude of the first response, or upon a time of travel of the particle from the first location to the second location.

39. The process of claim 28 wherein:
said first and second beams are inactive when in the second state.

40. The process of claim 28 wherein:
the first and second beams are in a low amplitude operating mode when in their respective second states.

41. The process of claim 28 wherein:
at least one of the first and second responses includes fluorescent energy of a plurality of different wavelengths emitted by the particle, and detecting the at least one of the responses includes separately sensing the different wavelengths of the fluorescent energy.

42. A particle characterizing apparatus with controllable coherent energy sources, including:
a flow generating device for moving a particle-containing fluid along a designated path to carry the particles serially along the path;
a first source adapted to generate a first coherent energy beam positioned to intersect the designated path at a first location for a first irradiation of each particle as it travels along the path, said first source being operable to adjust the first beam between a first state comprising a high amplitude operating mode, and a second state comprising either a low amplitude operating mode or an inactive state, wherein the first source further is adapted to maintain the first beam primarily in the first state;
a second source adapted to generate a second coherent energy beam positioned to intersect the designated path at a second location downstream of the first location for a second irradiation of each particle as it travels along the path, said second source being operable to adjust the second beam between a first state comprising a high amplitude operating mode, and a second state comprising either a low amplitude operating mode or an inactive state;
a sensing component for detecting a first response comprising radiant energy emanating from the particle in response to the first irradiation, and adapted to generate a first signal upon said detecting; and
a control channel coupled to the sensing component to receive the first signal and coupled to the first source, adapted to cause the first source to switch the first beam from the first state to the second state in response to receiving the first signal.

43. The apparatus of claim 42 wherein:
the second source is adapted to maintain the second beam primarily in the second state, and the control channel further is coupled to the second source and adapted to cause the second source to switch the second beam from the second state to the first state in response to receiving the first signal.

44. The apparatus of claim 43 wherein:
the control channel further is adapted to cause the first and second sources to effect said switching at the end of a predetermined delay following receipt of the first signal.

45. The apparatus of claim 43 wherein:
the sensing component further is adapted to detect a second response comprising radiant energy emanating from the particle in response to the second irradiation, and to generate a second signal upon said detection.

46. The apparatus of claim 45 wherein:
the control channel further is coupled to receive the second signal, and adapted to cause the first source to reset the first beam to the first state, and further to cause the second source to reset the second beam from the first state to the second state, in response to receiving the second signal.

47. The apparatus of claim 45 wherein:
the sensing component consists of a single detector.

48. The apparatus of claim 45 wherein:
the sensing component includes a first sensor for detecting the first response, and at least one second detector for detecting the second response.

49. The apparatus of claim 45 wherein:
the sensing component is adapted to determine an intensity of at least one of the first and second responses, to indicate a size of the particle.

50. The apparatus of claim 42 further including:
a timing device for measuring a time of travel for the particle from the first location to the second location as an indication of particle size.

51. The apparatus of claim 42 wherein:
the first and second sources are controllable to respectively reduce the amplitudes of the first and second beams in their respective second states.

52. The apparatus of claim 42 wherein:
the first and second sources are controllable to deactivate the first and second beams to their respective second states.

53. The apparatus of claim 45 wherein:
at least one of the first and second responses comprises a plurality of different fluorescent energy wavelengths, and the sensing component includes a plurality of different channels to individually sense the different wavelengths.

54. A particle detection apparatus, including:
a flow generating device for moving multiple particles serially along a predetermined path;
a coherent energy source for causing a first beam having a first wavelength to intersect the predetermined path at a first location;
a coherent energy source for causing a second beam to intersect the predetermined path at a second location, the second beam having a second wavelength shorter than the first wavelength and selected to trigger a responsive emission dependent on particle composition; and
a detector disposed proximate the predetermined path to detect energy at the first wavelength scattered by the particle as it travels past the first location, and to detect energy including a third wavelength emitted by the particle in response to irradiation by the second beam as it travels past the second location;
wherein the third wavelength is longer than the second wavelength.

55. The apparatus of claim 54 wherein:
the detector is sensitive to the first wavelength and the third wavelength, and substantially insensitive to the second wavelength.

56. The apparatus of claim 54 wherein:
the detector is sensitive to fluorescent energy, and the energy emitted by the particle is fluorescent energy.

57. The apparatus of claim 54 further including:
a particle sizing component including at least one of: a means for measuring an intensity of at least one of the scattered energy and the emitted energy at the detector;

and a means for determining a time of travel of the particle between the first and second locations.

58. The apparatus of claim 54 further including:
a control component for deactivating the first beam in response to sensing the scattered energy.

59. The apparatus of claim 58 wherein:
the control component is adapted to maintain the second beam primarily in an inactive state, and to activate the second beam in response to the sensing of the scattered energy.

60. The apparatus of claim 54 wherein:
the second location is downstream of the first location.

61. In an aerosol characterizing system including a first radiant energy beam irradiating aerosol particles at a first location along a path, a second radiant energy beam for irradiating the aerosol particles as they travel past a second location downstream of the first location, a first sensor adapted to detect energy scattered by the particles as they pass the first location and generating a first sensor output that varies with intensity of scattered energy, and a second sensor for detecting fluorescent energy emitted by each particle at the second location in response to irradiation by the second beam and generating a second output that varies with intensity of the fluorescent energy; a process for dynamically controlling the second sensor output, including:
detecting an amplitude of the first sensor output;
detecting an amplitude of the second sensor output;
detecting an amplitude of the second beam; and either:
(i) reducing the amplitude of the second beam, in response to detecting the first sensor output at an amplitude that exceeds a given maximum;
(ii) reducing a gain of the second sensor, in response to detecting the first sensor output at an amplitude that exceeds the given maximum; or
(iii) increasing an amplitude of the second beam according to a substantially linear ramp function while simultaneously monitoring a selected one of the second sensor output and the second beam amplitude, and clamping the ramp function when reaching a given maximum associated with the selected one.

62. A particle sizing system, including:
a flow generating device for moving multiple particles serially along a predetermined path and causing the particles to accelerate along at least part of the path;
a coherent energy source for causing a first beam to intersect the predetermined path at a first location;
a coherent energy source for causing a second beam to intersect the predetermined path at a second location spaced apart from the first location;
a first sensor positioned to detect energy at the first wavelength emanating from each of the particles in response to irradiation by the first beam as it travels past the first location;
a second sensor positioned to detect energy at a second wavelength emanating from each of the particles in response to irradiation by the second beam as it travels past the second location, wherein the second wavelength is different from the first wavelength; and
a timing component for determining a time for each particle to travel between the first and second locations, based on the outputs of the first and second detectors, wherein the timing component is adapted to identify the output of an upstream one of the first and second detectors as a time measurement starting point and to identify the output of the other of the sensors as a time measurement ending point, based on the difference in wavelengths of the energy detected by the first and second sensors, respectively.

63. The process of claim 61 wherein:
the second sensor output is dynamically controlled by reducing the amplitude of the second beam in response to detecting the first sensor output at an amplitude that exceeds the given maximum.

64. The process of claim 61 wherein:
the second sensor output is dynamically controlled by reducing a gain of the second sensor in response to detecting the first sensor output at an amplitude that exceeds a given maximum.

65. The process of claim 61 wherein:
the second sensor output is dynamically controlled by increasing an amplitude of the second beam according to a substantially linear ramp function while simultaneously monitoring the second sensor output, and clamping the ramp function when reaching a given maximum second sensor output.

66. The process of claim 61 wherein:
the second sensor output is dynamically controlled by increasing an amplitude of the second beam according to a substantially linear ramp function while simultaneously monitoring the second beam amplitude, and clamping the ramp function when reaching a given maximum second beam amplitude.

67. The system of claim 62 wherein:
the first location along the predetermined path is upstream of the second location, and the first beam has a first wavelength longer than a second wavelength of the second beam.

68. The system of claim 67 wherein:
the first wavelength is at least as long as a minimum wavelength of coherent energy in the ultraviolet range.

69. The system of claim 67 wherein:
the first wavelength is at least as long as a minimum wavelength of coherent energy in the near infrared range.

70. The system of claim 62 wherein:
the first sensor is adapted to detect energy at the first wavelength scattered by each of the particles in response to irradiation by the first beam, and the second sensor is adapted to detect energy at the second wavelength scattered by each of the particles in response to irradiation by the second beam.

71. The system of claim 62 wherein:
the first sensor is adapted to detect energy at the first wavelength scattered by each of the particles in response to irradiation by the first beam, and the second sensor is adapted to detect energy at the second wavelength emitted by each of the particles in response to irradiation by the second beam.

\* \* \* \* \*